United States Patent
Mortensen et al.

(10) Patent No.: US 12,246,970 B2
(45) Date of Patent: Mar. 11, 2025

(54) CYANIDE ON DEMAND

(71) Applicant: HALDOR TOPSØE A/S, Kgs. Lyngby (DK)

(72) Inventors: Peter Mølgaard Mortensen, Roskilde (DK); Kasper Emil Larsen, Humlebæk (DK); Kim Aasberg-Petersen, Allerød (DK); Robert Klein, Roskilde (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 439 days.

(21) Appl. No.: 17/630,734

(22) PCT Filed: Sep. 24, 2020

(86) PCT No.: PCT/EP2020/076713
§ 371 (c)(1),
(2) Date: Jan. 27, 2022

(87) PCT Pub. No.: WO2021/063799
PCT Pub. Date: Apr. 8, 2021

(65) Prior Publication Data
US 2022/0259056 A1    Aug. 18, 2022

(30) Foreign Application Priority Data

Oct. 1, 2019  (DK) .................. PA 2019 01150
Dec. 6, 2019  (DK) .................. PA 2019 01433

(51) Int. Cl.
*C01C 3/02*   (2006.01)
*B01J 12/00*  (2006.01)
(Continued)

(52) U.S. Cl.
CPC .......... *C01C 3/0229* (2013.01); *B01J 12/007* (2013.01); *B01J 19/0013* (2013.01);
(Continued)

(58) Field of Classification Search
None
See application file for complete search history.

(56) References Cited

U.S. PATENT DOCUMENTS 3,499,947 A   3/1970  Johnson
4,157,356 A   6/1979  Bulford et al.
(Continued)

FOREIGN PATENT DOCUMENTS

CA   2427464 A1   4/1999
CN   1483133 A    3/2004
(Continued)

OTHER PUBLICATIONS

U.S. Appl. No. 17/046,475, Peter Mølgaard Mortensen, filed Oct. 9, 2020 (Cited herein as US Patent Application Publication No. 2021/0171344 A1 of Jun. 10, 2021).
(Continued)

*Primary Examiner* — Colin W. Slifka
(74) *Attorney, Agent, or Firm* — Boone IP Law

(57) ABSTRACT

A reactor system and a process for carrying out the reaction of a feed gas comprising an alkane such as methane, and ammonia to hydrogen cyanide and/or a nitrile are provided, where the heat for the endothermic reaction is provided by resistance heating. In particular, the reaction is the BMA (Blausäure aus Methan und Ammoniak) reaction.

10 Claims, 10 Drawing Sheets

(51) Int. Cl.
  *B01J 19/00* (2006.01)
  *B01J 19/24* (2006.01)
  *C07C 253/24* (2006.01)

(52) U.S. Cl.
  CPC ......... *B01J 19/2415* (2013.01); *C07C 253/24* (2013.01); *B01J 2219/00135* (2013.01); *B01J 2219/00155* (2013.01)

(56) References Cited

U.S. PATENT DOCUMENTS

| | | | |
|---|---|---|---|
| 4,520,224 | A | 5/1985 | Kamimura |
| 5,631,302 | A | 5/1997 | Koenig et al. |
| 5,827,901 | A | 10/1998 | Koenig et al. |
| 5,976,723 | A | 11/1999 | Boffito et al. |
| 6,322,757 | B1 | 11/2001 | Cohn et al. |
| 6,433,029 | B1 | 8/2002 | Fitzpatrick |
| 6,746,650 | B1 | 6/2004 | Lesieur |
| 7,960,441 | B2 | 6/2011 | Wolf |
| 8,568,581 | B2 | 10/2013 | Sivasankar et al. |
| 9,067,847 | B2 | 6/2015 | Bashir et al. |
| 11,214,488 | B2 | 1/2022 | Rueger |
| 2002/0051741 | A1 | 5/2002 | Abe et al. |
| 2002/0081253 | A1 | 6/2002 | Abe |
| 2002/0094312 | A1 | 7/2002 | Hanus et al. |
| 2002/0119084 | A1 | 8/2002 | Boneberg |
| 2004/0016650 | A1 | 1/2004 | Klug |
| 2004/0081875 | A1 | 4/2004 | Milliken et al. |
| 2004/0197246 | A1 | 10/2004 | Stevens et al. |
| 2004/0265225 | A1 | 12/2004 | Watson et al. |
| 2006/0116543 | A1 | 6/2006 | Bellet et al. |
| 2006/0124445 | A1 | 6/2006 | Abrecque et al. |
| 2006/0254141 | A1 | 11/2006 | Krause et al. |
| 2007/0045125 | A1 | 3/2007 | Hartvigsen et al. |
| 2008/0023338 | A1 | 1/2008 | Stoots et al. |
| 2008/0169449 | A1 | 7/2008 | Mundschau |
| 2009/0220390 | A1 | 9/2009 | Grouset |
| 2009/0235587 | A1 | 9/2009 | Hawkes et al. |
| 2009/0289227 | A1 | 11/2009 | Rising |
| 2009/0307975 | A1 | 12/2009 | Wolf |
| 2010/0111781 | A1 | 5/2010 | Takahashi et al. |
| 2010/0296984 | A1 | 11/2010 | Ando et al. |
| 2011/0020207 | A1 | 1/2011 | Siegert |
| 2011/0136027 | A1 | 6/2011 | Chen et al. |
| 2011/0253550 | A1 | 10/2011 | Hoffmann |
| 2011/0253551 | A1 | 10/2011 | Lane et al. |
| 2011/0293510 | A1 | 12/2011 | Grannell et al. |
| 2012/0228150 | A1 | 9/2012 | Kang et al. |
| 2012/0288776 | A1 | 11/2012 | Nagaosa |
| 2012/0326090 | A1 | 12/2012 | Han et al. |
| 2013/0345326 | A1 | 12/2013 | Bashir et al. |
| 2014/0272734 | A1 | 9/2014 | Braun et al. |
| 2014/0291162 | A1 | 10/2014 | Sala et al. |
| 2015/0129805 | A1 | 5/2015 | Karpenko et al. |
| 2015/0175509 | A1 | 6/2015 | Almqvist et al. |
| 2015/0299871 | A1 | 10/2015 | Chen et al. |
| 2016/0002036 | A1 | 1/2016 | Kolaczkowski et al. |
| 2016/0355932 | A1 | 12/2016 | Reytier et al. |
| 2017/0106360 | A1 | 4/2017 | Meriam |
| 2018/0066371 | A1 | 3/2018 | Hong et al. |
| 2018/0127668 | A1 | 5/2018 | Masel |
| 2018/0194632 | A1 | 7/2018 | Jakobsson et al. |
| 2019/0085250 | A1 | 3/2019 | Anzelmo et al. |
| 2019/0112187 | A1 | 4/2019 | Østberg et al. |
| 2019/0144376 | A1 | 5/2019 | Højlund Nielsen et al. |
| 2020/0095124 | A1 | 3/2020 | Rueger |
| 2020/0354216 | A1 | 11/2020 | Mortensen |
| 2021/0113983 | A1 | 4/2021 | Mortensen et al. |
| 2021/0171344 | A1 | 6/2021 | Mortensen et al. |
| 2021/0238035 | A1 | 8/2021 | Mortensen et al. |
| 2022/0081289 | A1 | 3/2022 | De Sarkar et al. |

FOREIGN PATENT DOCUMENTS

| | | |
|---|---|---|
| CN | 101177239 A | 5/2008 |
| CN | 105188903 A | 12/2015 |
| DE | 102005046746 A1 | 4/2007 |
| DE | 102013102969 A1 | 9/2014 |
| DE | 102013226126 A1 | 6/2015 |
| EP | 0025205 A1 | 3/1981 |
| EP | 2491998 A1 | 8/2012 |
| EP | 2955158 A1 | 12/2015 |
| EP | 3249027 A1 | 11/2017 |
| EP | 2874738 B1 | 9/2018 |
| EP | 3415661 A1 | 12/2018 |
| EP | 3472370 A1 | 4/2019 |
| EP | 3574991 A1 | 12/2019 |
| GB | 722025 A | 1/1955 |
| GB | 0915444 A | 1/1963 |
| GB | 1269311 A | 4/1972 |
| GB | 1338352 A | 11/1973 |
| GB | 2358148 A | 7/2001 |
| JP | S5218485 A | 2/1977 |
| JP | H5-6120 U | 1/1993 |
| JP | 2002201002 A | 7/2002 |
| JP | 2003226657 A | 8/2003 |
| JP | 2003320254 A | 11/2003 |
| JP | 2008001584 A | 1/2008 |
| JP | 2010195642 A | 9/2010 |
| JP | 2014-152219 A | 8/2014 |
| KR | 10-2009-0068427 A | 6/2009 |
| KR | 10-2018-0075285 A | 7/2018 |
| WO | 0076651 A1 | 12/2000 |
| WO | 2004091773 A1 | 10/2004 |
| WO | 2007048641 A2 | 5/2007 |
| WO | 2007088923 A1 | 8/2007 |
| WO | 2010/004300 A1 | 1/2010 |
| WO | 2012084609 A1 | 6/2012 |
| WO | 2013/131778 A2 | 9/2013 |
| WO | 2014099567 A1 | 6/2014 |
| WO | 2014/154253 A1 | 10/2014 |
| WO | 2014/180888 A1 | 11/2014 |
| WO | 2015/014527 A1 | 2/2015 |
| WO | 2016/091636 A1 | 6/2016 |
| WO | 2017/014635 A1 | 1/2017 |
| WO | 2017036794 A1 | 3/2017 |
| WO | 2017186612 A1 | 11/2017 |
| WO | 2017186615 A1 | 11/2017 |
| WO | 2018/206235 A1 | 11/2018 |
| WO | 2018/228723 A1 | 12/2018 |
| WO | 2019/110266 A1 | 6/2019 |
| WO | 2019/110267 A1 | 6/2019 |
| WO | 2019104375 A1 | 6/2019 |
| WO | 2019110268 A1 | 6/2019 |
| WO | 2019/228796 A1 | 12/2019 |
| WO | 2019/228797 A1 | 12/2019 |
| WO | 2019228798 A1 | 12/2019 |
| WO | 2020/008008 A1 | 1/2020 |
| WO | 2020/035574 A1 | 2/2020 |
| WO | 2020/208008 A1 | 10/2020 |

OTHER PUBLICATIONS

U.S. Appl. No. 17/636,945, Peter Mølgaard Mortensen, filed Feb. 21, 2022,

U.S. Appl. No. 17/637,539, Peter Mølgaard Mortensen, filed Feb. 23, 2022.

U.S. Appl. No. 17/638,423, Peter Mølgaard Mortensen, filed Feb. 25, 2022.

U.S. Appl. No. 17/641,293, Peter Mølgaard Mortensen, filed Mar. 8, 2022.

Aasberg-Petersen, K., et al., "Synthesis gas production for FT synthesis," Studies in Surface Science and Catalysis, vol. 152, Chapter 4, 2004, p. 258-405, Elsevier B.V., The Netherlands.

Boccuzzi et al., "FTIR study of methanol decomposition on gold catalyst for fuel Cells", Journal of Power Sources, vol. 118, No. 1-2, May 25, 2003, pp. 304-310.

Danish Search Report dated Mar. 27, 2020 issued by the Danish Patent and Trademark Office in Danish Patent Application No. PA 201901437. (9 pages).

Danish Search Report for Danish Application No. PA 2019 01145 dated Mar. 12, 2020 (7 pages).

(56) References Cited

OTHER PUBLICATIONS

Danish Search Report for Danish Application No. PA 2019 01432 dated Mar. 27, 2020 (10 pages).
Danish Search Report issued in corresponding Patent Application No. PA 2019 01434 dated May 27, 2020 (8 pages).
European Search Report dated Jul. 11, 2018, by the European Patent Office for European Application No. 18175366.6 (7 pages).
International Preliminary Report on Patentability received for PCT Patent Application No. PCT/EP2019/062423, mailed on Dec. 10, 2020, 8 pages.
International Preliminary Report on Patentability received for PCT Patent Application No. PCT/EP2019/062424, mailed on Dec. 10, 2020, 8 pages.
International Search Report and Written Opinion received for PCT Patent Application No. PCT/EP2019/062423, mailed on Aug. 26, 2019, 10 pages.
International Search Report and Written Opinion received for PCT Patent Application No. PCT/EP2020/076695, mailed on Nov. 23, 2020, 11 pages.
International Search Report and Written Opinion received for PCT Patent Application No. PCT/EP2020/076698, mailed on Nov. 26, 2020, 9 pages.
International Search Report and Written Opinion received for PCT Patent Application No. PCT/EP2020/076700, mailed on Nov. 26, 2020, 11 pages.
International Search Report and Written Opinion received for PCT Patent Application No. PCT/EP2020/076707, mailed on Nov. 27, 2020, 11 pages.
Wismann, Sebastian T., et al., "Electrified methane reforming: A compact approach to greener industrial hydrogen production," Science, May 24, 2019, p. 756-759, vol. 364, American Association for the Advancement of Science, Washington, D.C.
Keim, W., "Synthesis Gas Feedstock for Chemicals", American Chemical Society, Jan. 1, 1987, vol. 25, No. 10, pp. 1-16. (16 pages).
Kongas, Rainer, "Review-Electrochemical CO2 Reduction for CO Production: Comparison of Low- and High-Temperature Electrolysis Technologies", Journal of the Electrochemical Society, Feb. 14, 2020, 167:0044508. (12 pages).
Wang, Y., et al., "High temperature solid oxide H2O/Co2 co-electrolysis for syngas production", Fuel Processing Technology, Nov. 14, 2016, vol. 161, pp. 248-258. (12 pages).
Danish Search Report issued in corresponding Patent Application No. PA 2019 01324 dated May 27, 2020, 8 pages.
International Search Report (PCT/ISA/210) and Written Opinion (PCT/ISA/237) mailed on Feb. 23, 2021, by the European Patent Office as the International Searching Authority for International Application No. PCT/EP2020/081700. (20 Pages).
U.S. Appl. No. 17/776,142, Peter Mølgaard Mortensen, filed May 11, 2022.
International Search Report (PCT/ISA/210) and Written Opinion (PCT/ISA/237) mailed on Nov. 26, 2020, by the European Patent Office as the International Searching Authority for International Application No. PCT/EP2020/076713. (12 pages).
Danish Search Report issued in corresponding Danish Patent Application No. PA201901433 dated Apr. 15, 2020. (9 pages).
Zhou L et al., "Investigation of a novel porous anodic alumina plate for methane steam reforming: Hydrothermal stability, electrical heating possibility and reforming reactivity" International Journal of Hydrogen Energy, Elsevier Science Publishers B.V., Barking, GB, vol. 34, No. 2, Jan. 1, 2009, pp. 844-858, XP025893337.
U.S. Appl. No. 18/256,689, Christian Wix, filed Jun. 13, 2023.
Search Report dated Jan. 28, 2019, issued in the Danish Patent Application No. PA201800249, 9 pages.
Search Report dated Apr. 24, 2020, issued in the Danish Patent Application No. PA201901435, 9 pages.
International Search Report (PCT/ISA/210) and Written Opinion (PCT/ISA/237) dated Jul. 26, 2019, issued in the European patent Application No. PCT/EP2019/062424, 11 pages.
International Search Report (PCT/ISA/210) and Written Opinion (PCT/ISA/237) dated Nov. 26, 2020, issued in the European Patent Application No. PCT/EP2020/076704, 11 pages.
Xu et al., "Methane Steam Reforming, Methanation and Water-Gas Shift: I. Intrinsic Kinetics", American Institution of Chemical Engineers Journal, vol. 35, No. 1, Jan. 1989, pp. 88-96.
Bonis, L.J. and H.H. Hausner, Fundamental Phenomena in the Material Sciences, vol. 1: Sintering and Plastic Deformation, pp. v-101, 1964 (Year: 1964).
Technology for Application of Industrial Control Computers, pp. 303-304, Beijing: Chemical Engineering Press, May 1982.
Introduction to Energy Chemistry, Dong Guanghua, etc., p. 124, Xuzhouo: China University of Mining and Technology Press, Sep. 2018.
Office Action with English translation only, mailed on Oct. 11, 2024, by the Japanese Patent1 Application No. (2022-520209), 5 pages.

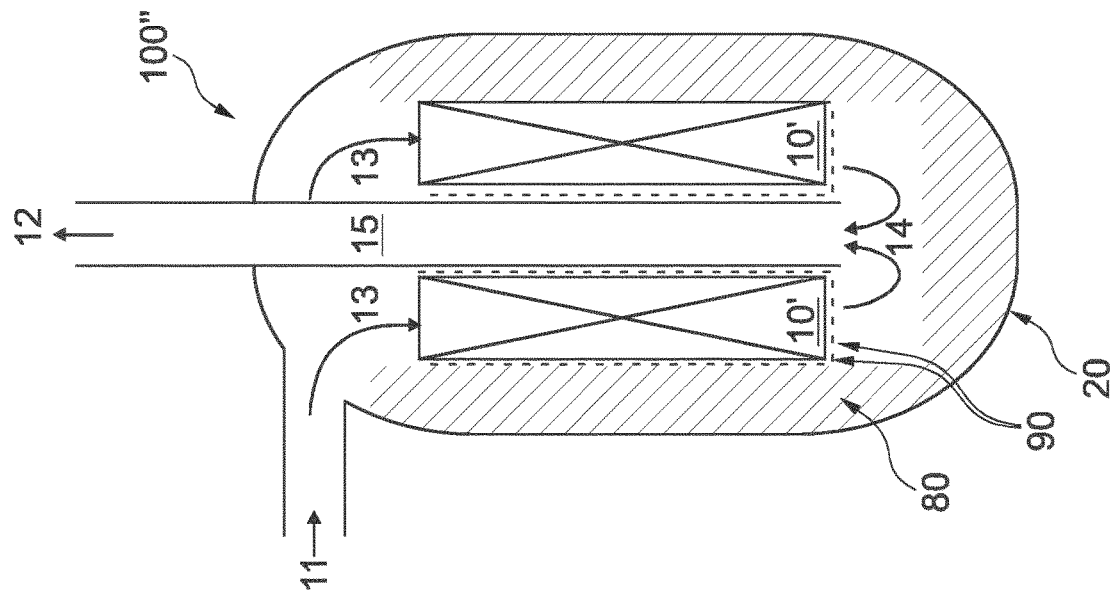
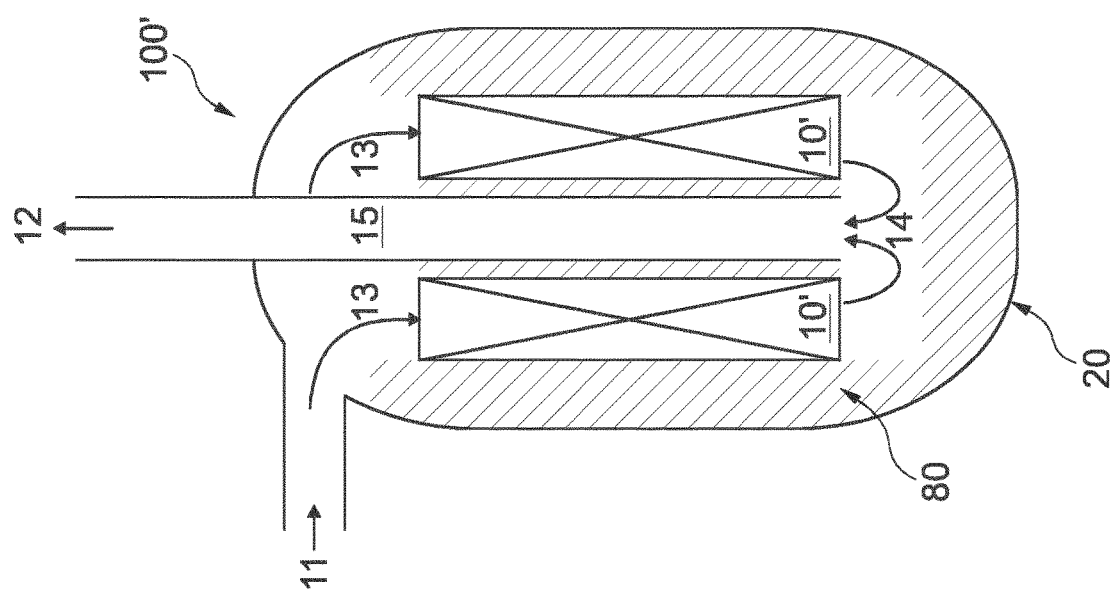

CYANIDE ON DEMAND

TECHNICAL FIELD

A reactor system and a process for carrying out the BMA (Blausäure aus Methan und Ammoniak; also called the Degussa process) reaction and/or nitrile synthesis of a feed gas comprising an alkane such as methane, and ammonia to hydrogen cyanide and/or a nitrile are provided, where the heat for the endothermic BMA reaction is provided by resistance heating.

BACKGROUND

Hydrogen cyanide is used in the chemical industry for the production of intermediate chemicals like acrylonitrile, methyl methacrylate, and adiponitrile. However, hydrogen cyanide HCN is difficult to produce, and often requires high temperature chemistry. A simple route for the production of cyanide is the BMA (Blausäure aus Methan und Ammoniak) process where methane and ammonia are reacted at around 1200-1300° C., typically in a fired reaction unit.

This process has, however, little industrial use with only 4 active plants in 2003, due to the high investment in the process compared to the relative small demand of hydrogen cyanide. Due to its high toxicity, there are strict regulations around the production, storage and transport of hydrogen cyanide.

It would therefore be desirable to produce hydrogen cyanide in an "on-demand" manner, at the site where it is required. Ideally, HCN production would be from readily-available starting materials which are cheap, safe and commonplace in industrial chemical plants. In this way, storage and transport of hydrogen cyanide could be reduced or even completely eliminated. Additionally, the possibility of rapid start-up and shut-down would also reduce the requirement for storage of HCN.

It is also desirable that the reactor system is compact and simple to operate equipment, allowing for less dangerous handling of hydrogen cyanide and/or nitriles. Another advantage of the technology is that the overall emission of carbon dioxide and other emissions detrimental to the climate may be reduced considerably, in particular if the power used in the reactor system is from renewable energy resources.

Systems and methods for steam methane reforming are set out in co-pending patent application PCT/EP2019/062423. Systems and methods for carrying out endothermic catalytic reactions are set out in co-pending patent application PCT/EP2019/062424.

SUMMARY

So, in a first aspect the present invention relates to a reactor system for carrying out the reaction (in particular the BMA reaction) of a feed gas comprising an alkane (in particular methane) and ammonia to hydrogen cyanide and/or a nitrile in the presence of a catalyst (in particular a BMA catalyst), e.g. under BMA reaction conditions, said reactor system comprising:

a supply of feed gas comprising an alkane such as methane and ammonia;
a structured catalyst arranged for catalyzing the reaction of said feed gas, said structured catalyst comprising a macroscopic structure of an electrically conductive material, said macroscopic structure supporting a ceramic coating, wherein said ceramic coating supports a catalytically active material;
a pressure shell housing said structured catalyst, said pressure shell comprising an inlet for letting in said feed gas and an outlet for letting out product gas, wherein said inlet is positioned so that said feed gas enters said structured catalyst in a first end of said structured catalyst and said product gas exits said structured catalyst from a second end of said structured catalyst;
a heat insulation layer between said structured catalyst and said pressure shell;
at least two conductors electrically connected to said structured catalyst and to an electrical power supply placed outside said pressure shell, wherein said electrical power supply is dimensioned to heat at least part of said structured catalyst to a temperature of at least 500° C. by passing an electrical current through said macroscopic structure, wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors;
an outlet for a product stream comprising hydrogen cyanide and/or a nitrile.

In a further aspect, a process is provided for carrying out the reaction of a feed gas comprising an alkane such as methane, and ammonia to hydrogen cyanide and/or a nitrile in the presence of a catalyst (e.g. under BMA reaction conditions), in a reactor system comprising a pressure shell housing a structured catalyst arranged for catalyzing said endothermic reaction of a feed gas, said structured catalyst comprising a macroscopic structure of electrically conductive material, said macroscopic structure supporting a ceramic coating, wherein said ceramic coating supports a catalytically active material; wherein said reactor system is provided with heat insulation between said structured catalyst and said pressure shell; said process comprising the steps of:

pressurizing said feed gas,
supplying said pressurized feed gas to said pressure shell through an inlet positioned so that said feed gas enters said structured catalyst in a first end of said structured catalyst; allowing the feed gas to undergo reaction over the structured catalyst and outletting a product gas from said pressure shell, wherein said product gas exits said structured catalyst from a second end of said structured catalyst;
supplying electrical power via electrical conductors connecting an electrical power supply placed outside said pressure shell to said structured catalyst, allowing an electrical current to run through said macroscopic structure, thereby heating at least part of the structured catalyst to a temperature of at least 500° C., wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors, thereby heating at least part of the structured catalyst to a temperature sufficient for said feed gas to undergo the BMA reaction over the structured catalyst, and outletting a product gas comprising hydrogen cyanide and/or a nitrile from the reactor system.

In a further aspect, a method is provided for rapidly switching a metal-catalysed reaction of a feed gas comprising an alkane such as methane, and ammonia in a reactor system as set out herein, from a first steady-state reaction condition (A) to a second steady-state reaction condition (B) or vice-versa; said method comprising the steps of:

in said first steady-state reaction condition (A):

supplying said feed gas to the reactor system in a first total flow, and supplying a first electrical power via electrical conductors connecting an electrical power supply placed outside said pressure shell to said structured catalyst, thereby allowing a first electrical current to run through said electrically conductive material, thereby heating at least part of the structured catalyst to a first temperature at which said feed gas is converted to a first product gas mixture over said structured catalyst under said first steady-state reaction conditions (A); and said first product gas is outlet from the reactor system;

and, in said second steady-state reaction condition (B):

supplying said feed gas to the reactor system in a second total flow, supplying a second electrical power via electrical conductors connecting an electrical power supply placed outside said pressure shell to said structured catalyst, thereby allowing a second electrical current to run through said electrically conductive material, thereby heating at least part of the structured catalyst to a second temperature; at which said feed gas is converted to a second product gas mixture over said structured catalyst under said second steady-state reaction conditions (B); and said second product gas is outlet from the reactor system; wherein said second electrical power is higher than said first electrical power; and/or said second total flow is higher than said first total flow.

Additional aspects of the invention are set out in the following detailed description, the examples and the appended claims.

LEGENDS TO THE FIGURES

FIGS. 3a and 3b show schematic cross sections through an embodiment of the inventive reactor system comprising a structured catalyst;

DETAILED DISCLOSURE

Figure 1A:
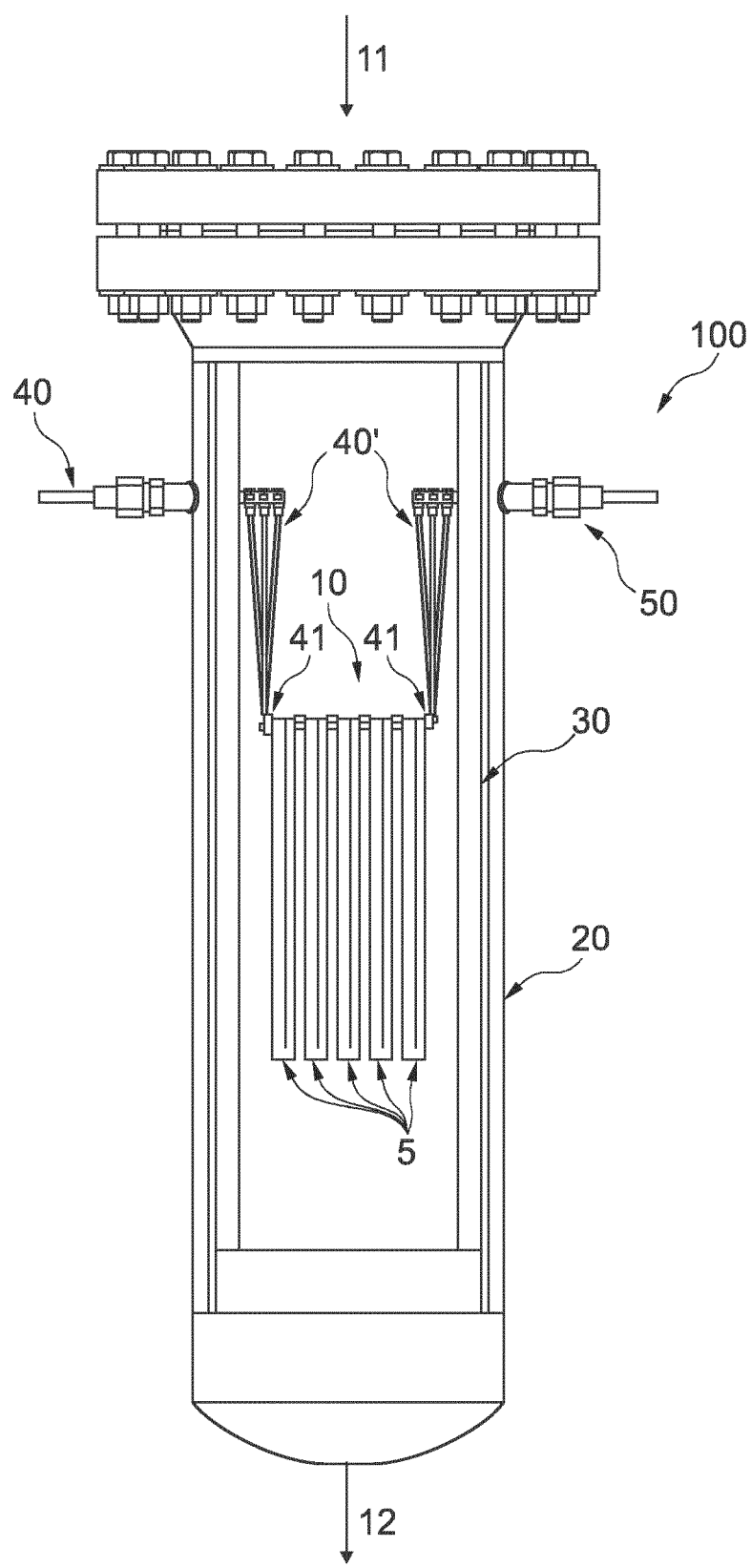
FIG. 1a shows a cross section through an embodiment of the inventive reactor system with a structured catalyst comprising an array of macroscopic structures, in a cross section.

The present technology describes how an electrically heated reactor can facilitate the task of producing hydrogen cyanide and/or nitriles via reaction in a compact design in an on-demand approach.

The present technology can be used to synthesis hydrogen cyanide (HCN) and/or nitriles (RCN, in which R is an alkyl group). When the alkane is methane, the catalyst is a BMA catalyst and the product stream comprises hydrogen cyanide.

However, when the alkane is ethane or propane, nitriles can be produced under similar principles, e.g.

$$2C_2H_6 + 2NH_3 \leftrightharpoons 2CH_3CN + 3H_2$$

$$2C_3H_8 + 2NH_3 \leftrightharpoons 2CH_3CH_2CN + 3H_2$$

If the feed gas comprises a mixture of methane and other alkanes, a product gas comprising product gas comprising hydrogen cyanide and/or a nitrile is obtained. In the following, the invention will be described for the synthesis of HCN via the BMA reaction. However, the technology is equally suitable for the synthesis of nitriles from alkanes, as set out above.

The BMA reaction can be summarised as:

$$CH_4 + NH_3 \leftrightharpoons HCN + 3\,H_2$$

in which the $\Delta H_R = 251$ kJ/mol. Typically, a platinium (Pt) catalyst is used as catalytically active material. The BMA process does not require $O_2$ (e.g. as the Andrussow process does). Therefore, in the present technology, the feed gas does not typically comprise oxygen.

A compact electric reactor using monolithic catalyst can easily be operated and use easy start-up principles to produce HCN when needed. This gives a relative inexpensive plant where HCN can be produced in only the required amounts and little to no HCN storage is needed, while transport of HCN also is reduced or completely eliminated. Simple reactor equipment and simple operation of the BMA process makes HCN production attractive in delocalized plants which reduce risks of HCN handling.

Additionally, the use of electricity as a heat source allows rapid start-up and shut-down (with a matter of minutes). This almost instantaneous switch from stand-by to HCN production and vice-versa also reduces the requirement for storage of HCN.

A reactor system for carrying out the reaction of a feed gas comprising an alkane such as methane, and ammonia to hydrogen cyanide and/or a nitrile in the presence of a catalyst such as BMA catalyst (e.g. under BMA reaction conditions) is thus provided, the reactor system comprising:

a supply of feed gas comprising an alkane and ammonia;

a structured catalyst arranged for catalyzing the reaction of said feed gas, said structured catalyst comprising a macroscopic structure of electrically conductive material, said macroscopic structure supporting a ceramic coating, wherein said ceramic coating supports a catalytically active material;

a pressure shell housing said structured catalyst, said pressure shell comprising an inlet for letting in said feed gas and an outlet for letting out product gas, wherein said inlet is positioned so that said feed gas enters said structured catalyst in a first end of said structured catalyst and said product gas exits said structured catalyst from a second end of said structured catalyst;

a heat insulation layer between said structured catalyst and said pressure shell;

at least two conductors electrically connected to said structured catalyst and to an electrical power supply placed outside said pressure shell, wherein said electrical power supply is dimensioned to heat at least part of said structured catalyst to a temperature of at least 500° C. by passing an electrical current through said macroscopic structure, wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors;

an outlet for a product stream comprising hydrogen cyanide and/or a nitrile.

In one preferred aspect, the alkane is methane, the catalyst is a BMA catalyst and the product stream comprises hydrogen cyanide.

The layout of the reactor system allows for feeding a pressurized feed gas to the reactor system at an inlet and directing this gas into the pressure shell of the reactor system. Inside the pressure shell, a configuration of heat insulation layers and inert material is arranged to direct the feed gas through the structured catalyst where it will be in contact with the catalyst material, where the catalytically active material will facilitate the BMA reaction. Additionally, the heating of the structured catalyst will supply the required heat for the endothermic reaction. The product gas from the heated structured catalyst is led to the reactor system outlet.

The close proximity between the catalytically active material and the electrically conductive materials enables efficient heating of the catalytically active material by close proximity heat conduction from the resistance heated electrically conductive material. An important feature of the resistance heating process is thus that the energy is supplied inside the object itself, instead of being supplied from an external heat source via heat conduction, convection and radiation. Moreover, the hottest part of the reactor system will be within the pressure shell of the reactor system. Preferably, the electrical power supply and the structured catalyst are dimensioned so that at least part of the structured catalyst reaches a temperature of at least 700° C., preferably at least 900° C., more preferably at least 1000° C. The surface area of the electrically conductive material, the fraction of the electrically conductive material coated with a ceramic coating, the type and structure of the ceramic coating, and the amount and composition of the catalytically active catalyst material may be tailored to the specific reaction at the given operating conditions.

The electrically conductive material is suitably a macroscopic structure. As used herein, the term "macroscopic structure" is meant to denote a structure that is large enough to be visible with the naked eye, without magnifying devices. The dimensions of the macroscopic structure are typically in the range of centimeters or even meters. Dimensions of the macroscopic structure are advantageously made to correspond at least partly to the inner dimensions of the pressure shell housing the structured catalyst, saving room for the heat insulation layer and conductors. Two or more macroscopic structures may be connected in order to provide an array of macroscopic structures having at least one of the outer dimensions in the range of meters, such as 2 m or 5 m. Such two or more macroscopic structures may be denoted "an array of macroscopic structures". In this case the dimensions of an array of macroscopic structures are advantageously made to correspond at least partly to the inner dimension of the pressure shell housing the structured catalyst (saving room for the heat insulation layer). A conceivable array of macroscopic structures could take up a volume of 0.1 to 10 m$^3$ or even larger. The structured catalyst may comprise a single macroscopic structure or an array of macroscopic structures, where the macroscopic structure(s) support(s) a ceramic coating supporting catalytically active material. In an array of macroscopic structures, the macroscopic structures may be electrically connected to each other; however, alternatively, the macroscopic structures are not electrically connected to each other. Thus, the structured catalyst may comprise two or more macroscopic structures positioned adjacent to each other. The macroscopic structure(s) may be extruded and sintered structures or 3D printed structures. A 3D printed macroscopic structure can be provided with or without subsequent sintering.

The physical dimensions of the macroscopic structure may be any appropriate dimensions; thus, the height may be smaller than the width of the macroscopic structure or vice versa.

The macroscopic structure supports a ceramic coating, where the ceramic coating supports a catalytically active material. The term "macroscopic structure supporting a ceramic coating" is meant to denote that the macroscopic structure is coated by the ceramic coating at, at least, a part of the surface of the macroscopic structure. Thus, the term does not imply that all the surface of the macroscopic structure is coated by the ceramic coating; in particular, at least the parts of the macroscopic structure which are electrically connected to the conductors do not have a coating thereon. The coating is a ceramic material with pores in the structure, which allows for supporting catalytically active material on and inside the coating. Advantageously, the catalytically active material comprises catalytically active particles having a size in the range from about 2 nm to about 250 nm.

Preferably, the macroscopic structure has been manufactured by extrusion of a mixture of powdered metallic particles and a binder to an extruded structure and subsequent sintering of the extruded structure, thereby providing a material with a high geometric surface area per volume. Preferably, the extruded structure is sintered in a reducing atmosphere to provide the macroscopic structure. Alternatively, the macroscopic structure is 3D printed a metal additive manufacturing melting process, viz. a 3D printing processes, which do not require subsequent sintering, such as powder bed fusion or direct energy deposition processes. Examples of such powder bed fusion or direct energy deposition processes are laser beam, electron beam or plasma 3D printing processes. As another alternative, the macroscopic structure may have been manufactured as a 3D metal structure by means of a binder-based metal additive manufacturing process, and subsequent sintered in a non-oxidizing atmosphere at a first temperature $T_1$, where $T_1 > 1000°$ C., in order to provide the macroscopic structure.

A ceramic coating, which may contain the catalytically active material, is provided onto the macroscopic structure before a second sintering in an oxidizing atmosphere, in order to form chemical bonds between the ceramic coating and the macroscopic structure. Alternatively, the catalytically active material may be impregnated onto the ceramic coating after the second sintering. When chemical bonds are formed between the ceramic coating and the macroscopic structure, an especially high heat conductivity between the electrically heated macroscopic structure and the catalytically active material supported by the ceramic coating is possible, offering close and nearly direct contact between the heat source and the catalytically active material of the structured catalyst. Due to close proximity between the heat source and the catalytically active material the heat transfer is effective, so that the structured catalyst can be very efficiently heated. A compact reactor system in terms of gas processing per reactor system volume is thus possible, and therefore the reactor system housing the structured catalyst may be compact.

As used herein, the terms "3D print" and "3D printing" is meant to denote a metal additive manufacturing process. Such metal additive manufacturing processes cover 3D printing processes in which material is joined to a structure under computer control to create a three-dimensional object, where the structure is to be solidified, e.g. by sintering, to provide the macroscopic structure. Moreover, such metal additive manufacturing processes cover 3D printing processes, which do not require subsequent sintering, such as powder bed fusion or direct energy deposition processes. Examples of such powder bed fusion or direct energy deposition processes are laser beam, electron beam or plasma 3D printing processes.

The reactor system does not need a furnace and this reduces the overall reactor size considerably.

The electrically conductive material comprises Fe, Ni, Cu, Co, Cr, Al, Si or an alloy thereof. Such an alloy may comprise further elements, such as Mn, Y, Zr, C, Co, Mo or combinations thereof. Preferably, the electrically conductive material comprises Fe, Cr, Al or an alloy thereof. Such an alloy may comprise further elements, such as Si, Mn, Y, Zr, C, Co, Mo or combinations thereof. Preferably, the catalytically active material is particles having a size from 2 nm to 250 nm. Preferably, the conductors and the electrically conductive material are made of different materials than the electrically conductive material. The conductors may for example be of iron, nickel, aluminum, copper, silver or an alloy thereof. The ceramic coating is an electrically insulating material and will typically have a thickness in the range of around 100 μm, say 10-500 μm.

The electrically conductive material is advantageously a coherent or consistently intra-connected material in order to achieve electrical conductivity throughout the electrically conductive material, and thereby achieve thermal conductivity throughout the structured catalyst and in particular providing heating of the catalyst material. By the coherent or consistently intra-connected material it is possible to ensure uniform distribution of current within the electrically conductive material and thus uniform distribution of heat within the structured catalyst. Throughout this text, the term "coherent" is meant to be synonymous to cohesive and thus refer to a material that is consistently intra-connected or consistently coupled. The effect of the structured catalyst being a coherent or consistently intra-connected material is that a control over the connectivity within the material of the structured catalyst and thus the conductivity of the electrically conductive material is obtained. It is to be noted that even if further modifications of the electrically conductive material are carried out, such as provision of slits within parts of the electrically conductive material or the implementation of insulating material within the electrically conductive material, the electrically conductive material is still denoted a coherent or consistently intra-connected material.

The gas flow over the structured catalyst may be axial or co-axial with the current path through the structured catalyst, perpendicular to the current path or have any other appropriate direction in relation to the current path.

The BMA reaction is highly endothermic. High temperatures typically in excess of 800-850° C. are needed to reach acceptable conversions of the methane in the feed.

The feedstock to the BMA reaction is preferably substantially pure streams of ammonia and methane. Alternatively, the methane is supplied in a hydrocarbon mixture supplied from e.g. natural gas or town gas, prospectively with an upstream upgrading step to remove the principle part of higher hydrocarbons and potential sulfur compounds typically present in such feedstocks. Also, the feedstock to the process may include recycle streams from unit operations downstream the reactor system. Such recycles might off-gases being rich in hydrogen generated from e.g. an upgrading unit arranged to purify the HCN of the product stream.

The feedstock for nitrile synthesis is preferably a substantially pure alkane like ethane, propane, or butane mixed with a substantially pure stream of ammonia.

In an embodiment, the alkane feedstock is a mixture of several alkanes mixed with a substantially pure stream of ammonia.

The term "electrically conductive" is meant to denote materials with an electrical resistivity in the range from: $10^{-5}$ to $10^{-8}$ Ω·m at 20° C. Thus, materials that are electrically conductive are e.g. metals like copper, silver, aluminum, chromium, iron, nickel, or alloys of metals. Moreover, the term "electrically insulating" is meant to denote materials with an electrical resistivity above 10 Ω·m at 20° C., e.g. in the range from $10^9$ to $10^{25}$ Ω·m at 20° C.

When the reactor system comprises a heat insulation layer between the structured catalyst and the pressure shell, appropriate heat and electrical insulation between the structured catalyst and the pressure shell is obtained. The presence of heat insulating layer between the pressure shell and the structured catalyst assists in avoiding excessive heating of the pressure shell, and assists in reducing thermal losses to the surroundings. The temperatures of the structured catalyst may reach up to about 1300° C., at least at some parts thereof, but by using the heat insulation layer between the structured catalyst and the pressure shell the temperature of the pressure shell can be kept at significantly lower temperatures of say 500° C. or even 100° C., which is advantageous as typical construction steel materials typically are unsuitable for pressure bearing application at temperatures above 1000° C. Moreover, a heat insulating layer between the pressure shell and the structured catalyst assists in control of the electrical current within the reactor system, since heat insulation layer is also electrically insulating. The heat insulation layer could be one or more layers of solid material, such as ceramics, inert material, fiber material, bricks or a gas barrier or a combination thereof. Thus, it is also conceivable that a purge gas or a confined gas constitutes or forms part of the heat insulation layer.

Moreover, it should be noted that the term "heat insulating material" is meant to denote materials having a thermal conductivity of about 10 W·m$^{-1}$·K$^{-1}$ or below. Examples of heat insulating materials are ceramics, bricks, alumina based materials, zirconia based materials and similar.

Advantageously, any relevant gaps between structured catalyst, the heat insulation layer, the pressure shell, and/or any other components inside the reactor system is filled with inert material, e.g. in the form of inert pellets. Such gaps are e.g. a gap between the lower side of the structured catalyst and the bottom of the pressure shell and a gap between the sides of the structured catalyst and the insulation layer covering the inner sides of the pressure shell. The inert material may e.g. be a ceramic material in the form of pellets or tiles. The inert material assists in controlling the gas distribution through the reactor system and in controlling the flow of the gas through the structured catalyst. Moreover, the inert material typically has a heat insulating effect.

The pressure shell suitably has a design pressure of between 2 bar and 30 bar. The actual operating pressure will be determined by the endothermic reaction, the size of the plants, among other aspects. As the hottest part of the reactor system is the electrically conductive material, which will be surrounded by heat insulation layer and within the pressure shell of the reactor system, the temperature of the pressure shell can be kept significantly lower than the maximum process temperature. This allows for having a relative low design temperature of the pressure shell of e.g. 700° C. or 500° C. or preferably 300° C. or 100° C. of the pressure shell whilst having maximum process temperatures of 400° C., or even 900, or even 1100° C., or even up to 1300° C. on the structured catalyst. Material strength is higher at the lower of these temperatures (corresponding to the design temperature of the pressure shell as indicated above). This offers advantages when designing the chemical reactor. Suitably, the pressure shell has a design pressure of between 2 bar and 30 bar, or between 30 and 200 bar. Around 30 bar is preferable as a compromise between process economy and thermodynamic limitations.

The resistivity of the electrically conductive material is suitably between $10^{-5}$ Ω·m and $10^{-7}$ Ω·m. A material with a resistivity within this range provides for an efficient heating of the structured catalyst when energized with a power source. Graphite has a resistivity of about $10^{-5}$ Ω·m at 20° C., kanthal has a resistivity of about $10^{-5}$ Ω·m at 20° C., whilst stainless steel has a resistivity of about $10^{-7}$ Ω·m at 20° C. The electrically conductive material may for example be made of FeCrAlloy having a resistivity of ca. $1.5 \cdot 10^{-6}$ Ω·m at 20° C.

Typically, the pressure shell comprises an inlet for letting in process gas and an outlet for letting out product gas, wherein the inlet is positioned close to a first end of the pressure shell and the outlet is positioned close to a second end of the pressure shell, and wherein the at least two conductors both are connected to the structured catalyst at a position on the structured catalyst closer to the inlet than to the outlet. Hereby, the at least two conductors can be placed in the substantially colder part of the reactor system as the inlet gas will have lower temperature than the product gas, the electrically conductive material will be colder in the most upstream part of the material due to the heat consumed by the progress of the chemical reaction, and the feed gas fed through the inlet may cool the at least two conductors before being heated by the heated structured catalyst further along the path of the gas over the heated structured catalyst. It is an advantage that the temperature of all electrically conducting elements except the electrically conductive material is kept down in order to protect the connections between the conductors and the structured catalyst. When the temperature of the conductors and other electrically conducting elements, except the electrically conductive material, is relatively low, less limitations on materials suitable for the conductors and other electrically conducting elements, except the electrically conductive material, exists. When the temperature of the electrically conducting elements increase, the resistivity thereof increases; therefore, it is desirable to avoid unnecessary heating of all other parts than the electrically conductive materials within the reactor system. The term "electrically conducting elements, except the electrically conductive material" is meant to cover the relevant electrically conducting elements arranged to connect the power supply to the structured catalyst, except the electrically conductive structured catalyst itself.

It should be noted, that the system of the invention may include any appropriate number of power supplies and any appropriate number of conductors connecting the power supply/supplies and the electrically conductive material(s) of the structured catalyst.

Suitably, the at least two conductors are led through a pressure shell in a fitting so that the at least two conductors are electrically insulated from the pressure shell. The fitting may be, partly, of a plastic and/or ceramic material. The term "fitting" is meant to denote a device that allows for mechanically connecting two pieces of hardware in a pressure bearing configuration. Thereby, the pressure within the pressure shell may be maintained even though the at least two conductors are lead through it. Non-limiting examples of the fittings may be an electrically insulating fitting, a dielectric fitting, a power compression seal, a compression fitting or a flange. The pressure shell typically comprises side walls, end walls, flanges and possibly further parts. The term "pressure shell" is meant to cover any of these components.

The pressure shell may further comprise one or more inlets close to or in combination with at least one of the fittings in order to allow a cooling gas to flow over, around, close to or inside at least one conductor within said pressure shell. Hereby, the conductors are cooled and thus the temperature that the fitting experiences is kept down. If the cooling gas is not used, the conductors may be heated by the feed gas to the reactor system, resistance heating of conductor due to the applied current, and/or heat conduction from the structured catalyst. The cooling gas could e.g. be hydrogen, argon, nitrogen, methane, ammonia or mixtures thereof. The temperature of the cooling gas at entry into the pressure shell may be e.g. about 100° C. or 200° C. or 250° C. In an embodiment, the conductor(s) is (are) hollow so that the cooling gas may flow through the conductor(s) and cool it (them) from within. By keeping the temperature of the fitting low, e.g. at around 100-200° C., it is easier to have a leak tight configuration. Typically, a part of the feed gas, such as one of the reactants, is fed to the pressure shell as the cooling gas. In another embodiment, part of the feed gas or a gas with the same composition as the feed gas is used as cooling gas.

The reactor system may further comprise an inner tube in heat exchange relationship with the structured catalyst, where the inner tube is adapted to withdraw a product gas from the structured catalyst so that the product gas flowing through the inner tube or tubes is in heat exchange relationship with the gas flowing over the structured catalyst, but electrically separated from the structured catalyst. This is a layout which here is denoted a bayonet reactor system. In this layout the product gas within the inner tube assists in heating the process gas flowing over the structured catalyst. The electrical insulation between the inner tube and the structured catalyst could be gas in the form of a gap or distance between the inner tube and the structured catalyst or inert material loaded around the inner tube and the structured catalyst. The gas may pass through the structured catalyst in an up-flow or a down-flow direction.

The connection between the structured catalyst and the at least two conductors may be a mechanical connection, a welded connection, a brazed connection or a combination thereof. The structured catalyst may comprise terminals physically and electrically connected to the structured catalyst in order to facilitate the electrical connection between the electrically conductive material and the at least two conductors. The term "mechanical connection" is meant to denote a connection where two components are held together mechanically, such as by a threaded connection or by clamping, so that a current may run between the components.

The electrically conductive materials placed in an array of electrically conductive materials may be electrically connected to each other. The connection between the two or more electrically conductive materials may be by mechanical connection, clamping, soldering, welding or any combination of these connection methods. Each electrically conductive material may comprise terminals in order to facilitate the electrical connections. The two or more electrically conductive materials may be connected to the power supply in serial or parallel connection. The electrical connection between the two or more electrically conductive materials is advantageously coherent and uniform along the connection surface between the two or more electrically conductive materials, so that the two or more electrically conductive materials act as a single coherent or consistently intra-connected material; hereby, uniform electrical conductivity throughout the two or more electrically conductive materials is facilitated. Alternatively, or additionally, the structured catalyst may comprise an array of electrically conductive materials that are not electrically connected to each other. Instead, two or more electrically conductive materials are placed together within the pressure shell, but not connected electrically to each other. In this case, the structured catalyst thus comprises electrically conductive materials connected in parallel to the power supply.

A ceramic coating, with or without catalytically active material, may be added directly to a metal surface of the electrically conductive material by wash coating. The wash coating of a metal surface is a well-known process; a description is given in e.g. Cybulski, A., and Moulijn, J. A., "Structured catalysts and reactors", Marcel Dekker, Inc, New York, 1998, Chapter 3, and references herein. The ceramic coat may be added to the surface of the electrically conductive material and subsequently the catalytically active material may be added; alternatively, the ceramic coat comprising the catalytically active material is added to the macroscopic structure or electrically conductive material. The ceramic coating may for example be an oxide comprising Al, Zr, Mg, Ce and/or Ca. Exemplary coatings are calcium aluminate or a magnesium aluminum spinel. Such a ceramic coating may comprise further elements, such as La, Y, Ti, K or combinations thereof. The ceramic coating is an electrically insulating material and will typically have a thickness in the range of around 100 μm, say 10-500 μm.

Extruding and sintering or 3D printing a macroscopic structure results in a uniformly and coherently shaped macroscopic structure, which can afterwards be coated with the ceramic coating.

The electrically conductive material and the ceramic coating may have been sintered in an oxidizing atmosphere in order to form chemical bonds between the ceramic coating and the electrically conductive material; this provides for an especially high heat conductivity between the electrically conductive material and the catalytically active material supported by the ceramic coating. Thereby, the structured catalyst is compact in terms of heat transfer to the active catalytic site, and a reactor system housing the structured catalyst may be compact and limited mainly by the rate of the chemical reaction.

In an embodiment, the structured catalyst has at least one electrically insulating part arranged to increase the current path between the conductors to a length larger than the largest dimension of the structured catalyst. The provision of a current path between the conductors larger than the largest dimension of the structured catalyst may be by provision of electrically insulating part(s) positioned between the conductors and preventing the current running through some part of the structured catalyst. Such electrically insulating parts are arranged to increase the current path and thus increase the resistance through the structured catalyst. Hereby, the current path through the structured catalyst can be e.g. more than 50%, 100%, 200%, 1000%, or even 10000% longer than the largest dimension of the structured catalyst.

Moreover, such electrically insulating parts are arranged to direct the current from one conductor, which is closer to the first end of the structured catalyst than to the second end, towards the second end of the structured catalyst and back to a second conductor closer to the first end of the structured catalyst than to the second end. Preferably, the current is arranged to run from the first end of the structured catalyst to the second and back to the first end. As seen in the figures, the first end of the structured catalyst is the top end thereof. The arrow indicated "z" in FIGS. 5-7 indicates a z-axis along the length of the structured catalyst. The principal current path throughout the structured catalyst will have a positive or negative value of z-coordinate of the accompanied current density vector along most of the length of the current path. By principal current path is meant the path of the electrons through a macroscopic structure of the structured catalyst with the highest current density. The principal current path can also be understood as the path having the minimum length through the macroscopic structure of the structured catalyst. Seen geometrically, the principal current path can be quantified as the largest current density vector within a plane perpendicular to the gas flow direction of a coherent section of the macroscopic structure. At the bottom of the structured catalyst, as shown in the figures, the current will turn, and here the z-coordinate of the accompanied current density vector will be zero.

As used herein, the term coherent section is meant to denote a cross-section area of the macroscopic structure wherein all walls of the coherent section are geometrically connected to one or more other walls of the coherent section within the same plane.

In an embodiment, the structured catalyst has at least one electrically insulating part arranged to direct a current through the structured catalyst in order to ensure that for at least 70% of the length of said structured catalyst, a current density vector of a principal current path has a non-zero component value parallel to the length of said structured catalyst. Thus, for at least 70% of the length of the structured catalyst, the current density vector will have a positive or negative component value parallel to the length of the structured catalyst. Thus, for at least 70%, e.g. for 90% or 95%, of the length of structured catalyst, viz. along the z-axis of the structured catalyst as seen in FIGS. 5 to 10, the current density vector of a principal current path will have a positive or negative value along the z-axis. This means that the current is forced from the first end of the structured catalyst towards the second end, and subsequently is forced towards the first end again. The temperature of the gas entering the first end of the structured catalyst and the endothermic BMA reaction taking place over the structured catalyst absorbs heat from the structured catalyst. For this reason, the first end of the structured catalyst remains colder than the second end, and by ensuring that the current density vector of the principal current path has a non-zero component value parallel to the length of said structured catalyst, this takes place with a substantially continuously increasing temperature profile, which gives a controllable reaction front. In an embodiment the current density vector has a non-zero component value parallel to the length of said structured catalyst in 70% of the length of said structured catalyst, preferably 80%, more preferably 90%, and even more preferably 95%. It should be noted that the term "the length of the structured catalyst" is meant to denote the dimension of the structured catalyst in the direction of the gas flow. In the structured catalysts as shown in the figures, the length is the longitudinal direction, viz. the longest dimension thereof. This is indicated by the arrow denote z in some of the figures.

Non-limiting examples of insulating parts are cuts, slits, or holes in the structure. Optionally, a solid insulating material such as ceramics in cuts or slits in the structure can be used. In a case where the solid insulating material is a porous ceramic material, the catalytically active material may advantageously be incorporated in the pores, by e.g. impregnation. A solid insulating material within a cut or slit assists in keeping the parts of the structured catalyst on the sides of the cut or slit from each other. As used herein, the term "largest dimension of the structured catalyst" is meant to denote the largest inner dimension of the geometrical form taken up by the structured catalyst. If the structured catalyst is box-formed, the largest dimension would be the diagonal from one corner to the farthest corner, also denoted the space diagonal.

It should be noted that even though the current through the structured catalyst may be arranged to twist or wind its way through the structured catalyst due to the electrically insulating parts arranged to increase the current path, the gas passing through the reactor system is inlet at one end of the reactor system, passes over the structured catalyst once before being outlet from the reactor system. Inert material is advantageously present in relevant gaps between the structured catalyst and the rest of the reactor system to ensure that the gas within the reactor system passes over the structured catalyst and the catalyst material herein.

The length of the gas passage through the structured catalyst is suitably less than the length of the passage of current from one electrode through the structured catalyst and to the next electrode. The ratio of the length of the gas passage to the length of the current passage may be less than 0.6, or 0.3, 0.1, or even down to 0.002.

Typically, the structured catalyst has electrically insulating parts arranged to make the current path through the structured catalyst a zigzag path. Here, the terms "zigzag path" and "zigzag route" is meant to denote a path that has corners at variable angles tracing a path from one conductor to another. A zigzag path is for example a path going upwards, turning, and subsequently going downwards. A zigzag path may have many turns, going upwards and subsequently downwards many times through the structured catalyst, even though one turn is enough to make the path a zigzag path.

It should be noted that the insulating parts arranged to increase the current path are not necessarily related to the ceramic coating on the electrically conductive material; even though this ceramic coating is also considered electrically insulating, it does not change the length of the current path between the conductors connected to the electrically conductive material.

The macroscopic structure may have a plurality of parallel channels, a plurality of non-parallel channels and/or a plurality of labyrinthine channels, where the channels have walls defining the channels. Thereby, several different forms of the macroscopic structure can be used as long as the surface area of the structured catalyst exposed to the gas is as large as possible. In a preferred embodiment, the macroscopic structure has parallel channels, since such parallel channels render a structured catalyst with a very small pressure drop. In a preferred embodiment, parallel longitudinal channels are skewed in the longitudinal direction of the macroscopic structure. In this way, molecules of the gas flowing through the macroscopic structure will mostly tend to hit a wall inside the channels instead of just flowing straight through a channel without being in contact with a wall. The dimension of the channels should be appropriate in order to provide a macroscopic structure with a sufficient resistivity. For example, the channels could be quadratic (as seen in cross section perpendicular to the channels) and have a side length of the squares of between 1 and 3 mm; however, channels having a maximum extent in the cross section of up to about 4 cm are conceivable. The walls may e.g. have a thickness of between 0.2 and 2 mm, such as about 0.5 mm, and the ceramic coating supported by the walls has a thickness of between 10 µm and 500 µm, such as between 50 µm and 200 µm, such as 100 µm. In another embodiment, the macroscopic structure of the structured catalyst is cross-corrugated.

In general, when the macroscopic structure is extruded or 3D printed, the pressure drop from the inlet to the outlet of the reactor system may be reduced considerably compared to a reactor where the catalyst material is in the form of pellets.

Suitably, the reactor system further comprises a bed of a second catalyst material upstream the structured catalyst within the pressure shell. Here, the term "upstream" is seen from the flow direction of the feed gas. Thus, the term "upstream" is here meant to denote that the feed gas is directed through the bed of second catalyst material prior to reaching the structured catalyst. This provides for a situation where the second catalyst material can be arranged for pre conditioning the feed stream. No specific heating needs to be provided to the bed of second catalyst material; however, the bed of second catalyst material may be heated indirectly if it is in close proximity to the structured catalyst. Alternatively, the second catalyst material may be heated. In order to clarify the terminology used here, it is noted that the term "structured catalyst" may also be denoted "a first catalyst material" to distinguish it from the second and/or third and/or fourth catalyst material.

The reactor system may further comprise a third catalyst material in the form of catalyst pellets, extrudates or granulates loaded into the channels of the macroscopic structure. In this embodiment, the reactor system will thus have a catalytically active material in the coating of the macroscopic structure as well as a third catalyst material in the form catalyst pellets, extrudates or granulates within the channels of the macroscopic structure. The pellets are e.g. prepared in a dimension to loosely match the size of channels to form a single string of pellets stacked upon each other within a channel of the macroscopic structure. Alternatively, the pellets, extrudates or granulates may be prepared in a dimension significantly smaller than the channel size to form a packed bed inside each channel. As used herein, the term "pellet" is meant to denote any well-defined structure having a maximum outer dimension in the range of millimeters or centimeters, while "extrudate" and "granulate" are meant to define a catalyst material with a maximum outer dimension defined within a range.

A bed of fourth catalyst material may be placed within the pressure shell and downstream the structured catalyst. Such fourth catalyst material may be in the form of catalyst pellets, extrudates or granulates.

Therefore the first, second, third, and fourth catalyst material may be catalyst materials suitable for the BMA reaction. In an embodiment this catalyst is $Pt/Al_2O_3$. In another embodiment it is $CoSn/Al_2O_3$. In a configuration where a combination of the second, third, and fourth catalyst material is included in the reactor system, the catalyst of each catalyst material can be different.

The geometric surface area of the macroscopic structure may be between 100 and 3000 $m^2/m^3$, such as between 500 and 1100 $m^2/m^3$. Typically, the material of the macroscopic structure is chosen as a material arranged to supply a heat flux of 500 $W/m^2$ to 50000 $W/m^2$ by resistance heating of the material. Preferably, resistance heating of the material supplies a heat flux of between 5 $kW/m^2$ and 12 $kW/m^2$, for example between 8 $kW/m^2$ and 10 $kW/m^2$. The heat flux is given as heat per geometric surface area of the surface exposed to the gas.

In an embodiment the structured catalyst comprises a first part arranged to generate a first heat flux and a second part arranged to generate a second heat flux, where the first heat flux is lower than the second heat flux, and where the first part is upstream the second part. Here, the term "the first part is upstream the second part" is meant to denote, that the gas fed into the reactor system reaches the first part before the gas reaches the second part. The first part and second part of the structured catalyst may be two different macroscopic structures supporting ceramic coating supporting catalytically active material, where the two different macroscopic structures may be arranged to generate different heat fluxes for a given electrical current and voltage. For instance, the first part of the structured catalyst may have a large surface area, whilst the second part of the structured catalyst has a smaller surface area. This may be accomplished by providing a structured catalyst in the second part having a smaller cross sectional area than the cross sectional area of the first part. Alternatively, the current path through the first part of the structured catalyst may be more straight than the current path through the second part of the structured catalyst, thus making the current twist and wind more through the second part than through the first part of the structured catalyst, whereby the current generates more heat in the second part of the structured catalyst than in the first part. As mentioned before, slits or cuts in the macroscopic structure may make the current path zigzag through the macroscopic structure. It should be noted, that the first and second part of the structured catalyst may experience different electrical currents and voltages in order to be able to supply different heat fluxes. However, the different heat fluxes of the first and second part may also be achieved by supplying the same electrical current and voltage through/over the first and second part, due to different physical properties of the first and second part as indicated above. In a further embodiment, the structured catalyst comprises a third part arranged to generate a third heat flux, where the third heat flux is lower than the first and/or the second heat flux, and where the third part is downstream the first and/or second part.

The predetermined temperature range of the gas exiting the pressure shell/the reactor system is the range from 200 to 1300° C. The product gas outlet temperature from the structured catalyst is measured directly beneath or on the most downstream surface of the structured catalyst. Measuring technology can be thermocouples (by voltage drop), resistance temperature detectors or infrared detection. The measuring point can be separated from the structured catalyst and be embedded in downstream inert/catalyst, or be directly on the surface with an insulating surface coverage.

The structured catalyst within said reactor system suitably has a ratio between the area equivalent diameter of a horizontal cross section through the structured catalyst and the height of the structured catalyst in the range from 0.1 to 2.0. The area equivalent diameter of the cross section through the reactor system is defined as the diameter of a circle of equivalent area as the area of the cross section. When the ratio between the area equivalent diameter and the height of the structured catalyst is between 0.1 and 2.0, the pressure shell housing the structured catalyst may be relatively small compared to other reactor systems for endothermic reactions such as a current tubular reformer for steam methane reforming.

Typically, the gas flows through the reactor system in an upflow or downflow direction, so that the gas flows through channels in the structured catalyst along the height thereof. When the structured catalyst comprises a number of or an array of macroscopic structures, the individual macroscopic structures within the array may be placed side by side, on top of each other or in a combination thereof. It is stressed that, when the structured catalyst comprises more than one macroscopic structures, the dimensions of the structured catalyst are the dimensions of the more than one macroscopic structures. Thus, as an example, if the structured catalyst comprises two macroscopic structures, each having the height h, put on top of each other, the height of the structured catalyst is 2h.

The volume of the structured catalyst is chosen in consideration of the desired feed conversion and/or temperature out of the reactor system correlated to the heat generation capacity of the electrically conductive material.

Suitably, the height of the reactor system is between 0.5 and 7 m, more preferably between 0.5 and 3 m. Exemplary values of the height of the reactor system is a height of less than 5 meters, preferably less than 2 m or even 1 m. The dimensions of the reactor system and of the structured catalyst within the reactor system are correlated; of course, the pressure shell and heat insulation layer render the reactor system somewhat larger than the structured catalyst itself.

The reactor system may further comprise an upgrading unit arranged to receive the product stream comprising hydrogen cyanide and separate it into an upgraded hydrogen cyanide stream and an off-gas stream.

The reaction system described above is—in contrast to a fired BMA reactor—not a segregated system. As heating is not transferred across a pressure bearing wall, the risk of mechanical failure is not high. From a catalyst point of view, temporary overheating is not a problem, it will just produce a very hot gas. This means that start-up is fast in comparison and in practice the current invention can be started by applying a given voltage and then the system will work towards a thermal equilibration to reach steady state without any additional operator input.

A process for carrying out the reaction of a feed gas comprising an alkane such as methane and ammonia to hydrogen cyanide and/or a nitrile in the presence of a catalyst such as a BMA catalyst (e.g. under BMA reaction conditions) is also provided, in a reactor system comprising a pressure shell housing a structured catalyst arranged for catalyzing said endothermic reaction of a feed gas, said structured catalyst comprising a macroscopic structure of electrically conductive material, said macroscopic structure supporting a ceramic coating, wherein said ceramic coating supports a catalytically active material; wherein said reactor system is provided with heat insulation between said structured catalyst and said pressure shell.

The process comprises the steps of:
pressurizing said feed gas,
supplying said pressurized feed gas to said pressure shell through an inlet positioned so that said feed gas enters said structured catalyst in a first end of said structured catalyst; allowing the feed gas to undergo reaction over the structured catalyst and outletting a product gas from said pressure shell, wherein said product gas exits said structured catalyst from a second end of said structured catalyst;
supplying electrical power via electrical conductors connecting an electrical power supply placed outside said pressure shell to said structured catalyst, allowing an electrical current to run through said macroscopic structure, thereby heating at least part of the structured catalyst to a temperature of at least 500° C., wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors, thereby heating at least part of the structured catalyst to a temperature sufficient for said feed gas to undergo the BMA reaction over the structured catalyst,
outletting a product gas comprising hydrogen cyanide and/or nitrile from the reactor system.

All details of the system given above are—wherever possible—relevant to the process described above.

In one aspect, the feed gas is pressurised to a pressure between 2 and 30 bar. The feed gas may be pressurised to a pressure between 30 and 200 bar. Suitably, at least part of the structured catalyst is heated to a temperature of at least 700° C., preferably at least 900° C., more preferably at least 1000° C. The maximum temperature to which the structured catalyst is heated is ca. 1400° C.

One aspect of the process further comprises the step of inletting a cooling gas through an inlet through the pressure shell in order to allow said cooling gas to flow over at least one conductor.

Suitably, in the process of the invention, the alkane is methane, the catalyst is a BMA catalyst and the product stream comprises hydrogen cyanide.

The process may further comprises the step of feeding the product stream comprising hydrogen cyanide to an upgrading unit and separating it into an upgraded hydrogen cyanide stream and an off-gas stream. The upgrading unit may be arranged so that the off-gas stream is recycled and mixed with the supply of feed gas before being passed over the structured catalyst.

The upgrading unit may comprise a combination of absorbers, scrubbers, strippers, and condensers. In an embodiment, the process gas from the reactor system is passed through a monoammonium phosphate solution to remove ammonia. The resulting stream is then passed to a HCN adsorber using cold water to retain HCN, and the solution is sent to a HCN stripper for product purification. In another embodiment, the process gas from the reactor system is passed through a sulphuric acid scrubber to remove ammonia. The resulting stream is then passed to a HCN adsorber using cold water to retain HCN, and the solution is sent to a HCN stripper for product purification.

In one aspect, the process further comprises the step of feeding the upgraded hydrogen cyanide stream from said upgrading unit to a downstream plant for HCN conversion to an upgraded product and where the production of HCN is equivalent to the consumption of HCN in the downstream plant. This means that the HCN is produced "on demand" such that there is no intermediate stock of HCN to be stored or transported. Examples of upgraded products include acetone cyanohydrin, adiponitrile, sodium cyanide, methionine, and cyanuric chloride.

A method for rapidly switching a metal-catalysed reaction of a feed gas comprising methane and ammonia in a reactor system as set out herein, from a first steady-state reaction condition (A) to a second steady-state reaction condition (B) or vice-versa, is therefore provided.

Reaching a steady state condition is defined as when central process parameters (such as feed flow, outlet temperature, and reactant conversion) have reached a value within ±15% of the average process value for the given process parameter for the subsequent hour.

A condition of the invention, A or B, involves a state where the catalyst of the system is heated by an electrical power balanced to heat the product gas outlet temperature from the structured catalyst to a temperature between 300 and 1300° C. at a pressure between 5 barg and 150 barg with a feedstock comprising methane and ammonia, and any of hydrogen, nitrogen, argon, or oxygen in a total flow rate of 300 Nm$^3$/h to 100 000 Nm$^3$/h. When the feedstock passes the monolith, it will react towards equilibration of the reaction.

In an embodiment of the invention, the method includes an initial reaction condition A where the feedstock consists of 49.6% $CH_4$, 49.6% $NH_3$, 0.2% $N_2$, and 0.6% $H_2$ in a total flow of 547 Nm$^3$/h having a temperature of 430° C. at a pressure of 6.7 barg. Supplying a first electrical power of 100 kW generates an almost equilibrated gas composed of 46.3% $CH_4$, 46.3% $NH_3$, 0.2% $N_2$, 5.6% $H_2$, and 1.7% HCN in a total flow of 566 Nm$^3$/h having a temperature of 600° C. at a pressure of 6.6 barg. Switching to condition B over a period of about 90 min while applying a second electrical power of 1090 kW generates an almost equilibrated gas composed of 5.0% $CH_4$, 5.0% $NH_3$, 0.1% $N_2$, 67.6% $H_2$, and 22.4% HCN in a total flow of 992 Nm$^3$/h having a temperature of 1130° C. at a pressure of 6.6 barg.

In an embodiment of the invention, the method includes an initial reaction condition A where the feedstock consists of 48.4% $CH_4$, 48.4% $NH_3$, 0.8% $N_2$, and 2.4% $H_2$ in a total flow of 127 Nm$^3$/h having a temperature of 430° C. at a pressure of 34.3 barg. Supplying a first electrical power of 200 kW generates an almost equilibrated gas composed of 13.0% $CH_4$, 13.0% $NH_3$, 0.5% $N_2$, 55.5% $H_2$, and 18.0% HCN in a total flow of 199 Nm$^3$/h having a temperature of 1150° C. at a pressure of 34.0 barg. Switching to condition B over a period of about 25 min while applying a second electrical power of 580 kW and increasing the total feed flow to 381 Nm$^3$/h, generates an almost equilibrated gas composed of 14.0% $CH_4$, 14.0% $NH_3$, 0.5% $N_2$, 54.1% $H_2$, and 17.5% HCN in a total flow of 586 Nm$^3$/h having a temperature of 1135° C. at a pressure of 34 barg.

The term "vice versa" is used to mean that the method applies equally when switching from the first reaction condition (A) to the second reaction condition (B) as when switching from the second reaction condition (B) to the first reaction condition (A). Notably, a switch from condition A to B is considered completed when the process values of the system have reached within 85% of steady state conditions.

The reactor system is as described above; i.e. it comprises a pressure shell housing a structured catalyst arranged to catalyze the reaction of a feed gas comprising methane and ammonia, said structured catalyst comprising a macroscopic structure of an electrically conductive material, said macroscopic structure supporting a ceramic coating, where said ceramic coating supports a catalytically active material and wherein said reactor system is provided with heat insulation between said structured catalyst and said pressure shell. All details described above in relation to the reactor system are relevant for the present technology.

The method of this aspect of the invention comprises the steps of:
in said first steady-state reaction condition (A):
supplying said feed gas to the reactor system in a first total flow, and
supplying a first electrical power via electrical conductors connecting an electrical power supply placed outside said pressure shell to said structured catalyst, thereby allowing a first electrical current to run through said electrically conductive material,
thereby heating at least part of the structured catalyst to a first temperature at which said feed gas is converted to a first product gas mixture over said structured catalyst under said first steady-state reaction conditions (A); and said first product gas is outlet from the reactor system;
and, in said second steady-state reaction condition (B):
supplying said feed gas to the reactor system in a second total flow,
supplying a second electrical power via electrical conductors connecting an electrical power supply placed outside said pressure shell to said structured catalyst, thereby allowing a second electrical current to run through said electrically conductive material,
thereby heating at least part of the structured catalyst to a second temperature; at which said feed gas is converted to a second product gas mixture over said structured catalyst under said second steady-state reaction conditions (B); and said second product gas is outlet from the reactor system;
To achieve the first and second steady-state reaction conditions (A) and (B), the second electrical power is higher than said first electrical power; and/or said second total flow is higher than said first total flow.

Notably, an increase in total flow will increase the input of cool feed gas, thus cooling the structured catalyst, and reducing the reactivity so that second steady-state reaction condition (B) is achieved. A significant change in flow will change the energy required for the process.

A change in total flow may include a change in total flow with no compositional change or a change in the composition, such as increasing recycle flow or changing part of the feedstock.

In one embodiment, the ratio of total gas feed flow in said first reaction condition A to said second reaction condition B (A:B) is at least 1:10. Switching between condition A and B consequently allows for significant increased/decreased production of product gas. This is advantageous when the invention is used for e.g. energy storage where excess electric energy from the energy grid is available and in this way can be stored as chemical energy, or vice versa for increasing availability of electric energy in the grid when it is needed elsewhere. Additionally, the embodiment allows for using the invention to supply large amounts of product gas in periods where downstream processes demands it, while having the invention operating in a standby condition otherwise. This is advantageously if there is no continuous demand for the product gas.

In another embodiment, the product gas outlet temperature from the structured catalyst in reaction condition B is between 50° C. to 800° C. higher, such as between 100° C. to 500° C. higher, preferably between 150° C. to 400° C. higher, than the product gas outlet temperature from the structured catalyst in reaction condition A. This allows for rapidly starting up the reactor system from a cold state to operating conditions. This is advantageously in the situation of system start-up, where the start-up procedure involves steps including:
Heating process equipment in a non-condensing gas to a temperature above the condensation point of the steady state conditions of the plant at full operating capacity,
Pressurising the feed gas constituents,
Feeding feed gas constituents to the reactor system while applying a first electrical power,
Switching to a higher operating temperature by applying a second electrical power.

In this way, all steps of the start-up procedure are relatively fast.

The product gas outlet temperature from the structured catalyst in reaction condition B is typically no more than 50° C. higher than the product gas outlet temperature from the structured catalyst in reaction condition A. This allows for rapidly changing the between condition A and B, without significantly changing the product gas composition from the system. In this way, the demand for the product gas for downstream processes of the reactor system can easily be supplied in different quantities without interfering significantly in the chemical environment of these.

In one embodiment, the switch between reaction condition A and B includes a gradual change of the total gas feed flow from said first total flow to said second total flow and simultaneous gradual change of the applied electrical potential over said electrically conductive material from said first to said second electrical power. In this way, the product gas composition can be held almost constant also during the transition stage. In an embodiment, the gradual changes are made in such a way where the flow is increased in small steps while increasing the electrical power to maintain an almost constant product gas outlet temperature from the structured catalyst.

In an embodiment, the reactor system further comprises a control system arranged to control the electrical power supply to ensure that the temperature of the gas exiting the pressure shell lies in a predetermined range and/or to ensure that the conversion of the feed gas lies in a predetermined range. The control of the electrical power supply is the control of the electrical output from the power supply. The control of the electrical power supply may e.g. be carried out as a control of the voltage and/or current from the electrical power supply, as a control of whether the electrical power supply is turned on or off or as a combination hereof. The power supplied to the structured catalyst can be in the form of alternating current or direct current.

According to one embodiment, a proportional-integral-derivative (PID) controller controls the electrical potential based on feedback reading of the process value of product gas outlet temperature from the structured catalyst.

The method described herein allows rapid switching between conditions A and B. Suitably, therefore, the switch between reaction conditions A and B takes place over a period of less than 3 hours, such as less than 2 hours, such as less than 60 min, preferably less than 30 min, and even more preferably less than 15 min.

In one embodiment, the switch between reaction condition A and B involves supplying a second electrical power to the structured catalyst. This suitably occurs while keeping the total flow essentially constant.

In one aspect, the switch between reaction condition A and B comprises a transition state between said reaction conditions A and B; said transition state comprising a first period in which the electrical power is switched off, followed by a second period in which said second electrical power of condition B is supplied to the structured catalyst. This allows for faster establishment of a steady state.

In one aspect, the switch between reaction condition A and B comprises a transition state between said reaction conditions A and B; said transition state comprising a first period in which a third electrical power is supplied to the structured catalyst, followed by a second period in which said second electrical power of condition B is supplied to the structured catalyst, said third electrical power being higher than the second electrical power. This allows for faster establishment of a steady state.

The process may comprise further steps carried out on the product gas comprising hydrogen cyanide, such as purification, pressurization, heating, cooling, etc. to provide the final product gas for an application downstream the reactor system of this invention.

It should be noted that the feed gas may comprises individual feed gasses and that the step of pressurizing the feed gas may comprise pressurizing individual feed gasses individually. Moreover, it should be noted that the order in which the steps of the process are written are not necessarily the order in which the process steps take place, in that two or more steps may take place simultaneously, or the order may be different that indicated above.

In an embodiment, the process comprises the step of pressurizing the gas upstream the pressure shell to a pressure of up to at least 2 bar. The chosen operating pressure is defined by the endothermic reaction and the integration of the reactor in the surrounding process steps.

In an embodiment of the process according to the invention, the temperature of the feed gas let into the reactor system is between 100° C. and 700° C. However, in all embodiments the temperature and the pressure of the feed gas are adjusted to ensure that the feed gas is above the dew point.

In an embodiment of the process of the invention, the structured catalyst is heated so that the maximum temperature of the structured catalyst lies between 200° C. and 1300° C. The used temperature will be dependent on the endothermic reaction. The maximum temperature of the structured catalyst depends upon the material of the electrically conductive material; thus, if the electrically conductive material is of FeCrAlloy, which melts at a temperature of between 1380° C. and 1490° C. (depending on the actual alloy), the maximum temperature should be somewhat below the melting point, such as at about 1300° C. if the melting point of the electrically conductive material is at about 1400° C., as the material will become soft and ductile when approaching the melting point. The maximum temperature may additionally be limited by the durability of the catalyst material, the coating and the catalytically active material.

In an embodiment the process according to the invention further comprises the step of inletting a cooling gas through an inlet through the pressure shell in order to allow a cooling gas to flow over at least one conductor and/or fitting. The cooling gas may advantageously be hydrogen, nitrogen, ammonia, methane or any other gas suitable for cooling the area or zone around the at least one conductor. A part of the feed gas may be fed to the pressure shell as the cooling gas.

In an embodiment according to the invention, the process further comprises the step of inletting a cooling gas through an inlet through the pressure shell in order to allow a cooling gas to flow over at least one conductor and/or fitting. The cooling gas may be any appropriate gas; examples of such gasses are hydrogen, nitrogen, ammonia, methane or mixtures thereof. The cooling gas may flow through the conductor(s) and cool it (them) from within; in this case, the conductor(s) need(s) to be hollow to accommodate the cooling gas flowing within it/them.

The catalyst material for the reaction may be $Pt/Al_2O_3$, $Pt/ZrO_2$, $Ru/Al_2O_3$, $Rh/Al_2O_3$, $Pt/MgAl_2O_3$, or $CoSn/Al_2O_3$. The catalytically active material may be Pt, Ru, Rh, Ir, Co, Sn, or a combination thereof, while the ceramic coating may be $Al_2O_3$, $ZrO_2$, $MgAl_2O_3$, $CaAl_2O_3$, or a combination therefore and potentially mixed with oxides of Y, Ti, La, or Ce. The maximum temperature of the reactor may be between 850-1300° C. The pressure of the feed gas may be 2-180 bar, preferably about 25 bar. In an embodiment said macroscopic structure is made of an alloy of Fe Cr Al, supporting a ceramic coating of a $ZrO_2$ and $Al_2O_3$ mixture, with Pt as catalytically active material.

DETAILED DESCRIPTION OF THE FIGURES

In the following description of the figures, the BMA reaction is described. However, the details of the reactor system etc. also apply to nitrile synthesis.

Throughout the Figures, like reference numbers denote like elements.

FIG. 1a shows a cross section through an embodiment of a reactor system 100 according to the invention. The reactor system 100 comprises a structured catalyst 10, arranged as an array of macroscopic structures 5. Each macroscopic structure 5 in the array is coated with a ceramic coating impregnated with catalytically active material. The reactor system 100 moreover comprises conductors 40, 40' connected to a power supply (not shown in the Figures) and to the structured catalyst 10, viz. the array of macroscopic structures. The conductors 40, 40' are led through the wall of a pressure shell 20 housing the structured catalyst and through insulating material 30 on the inner side of the pressure shell, via fittings 50. The conductors 40' are connected to the array of macroscopic structures 5 by conductor contact rails 41.

In an embodiment, the electrical power supply supplies a voltage of 26V and a current of 1200 A. In another embodiment, the electrical power supply supplies a voltage of 5V and a current of 240 A. The current is led through electrical conductors 40, 40' to conductor contact rails 41, and the current runs through the structured catalyst 10 from one conductor contact rail 41, e.g. from the conductor contact rail seen to the left in FIG. 1a, to the other conductor contact rail 41, e.g. the conductor contact rail seen to the right in FIG. 1a. The current can be both alternating current, and e.g. run alternating in both directions, or direct current and run in any of the two directions.

The macroscopic structures 5 are made of electrically conductive material. Especially preferred is the alloy kanthal consisting of aluminum, iron and chrome. The ceramic coating, e.g. an oxide, coated onto the structure catalysts 5 is impregnated with catalytically active material. The conductors 40, 40' are made in materials like iron, aluminum, nickel, copper or alloys thereof.

During operating, a feed gas comprising methane and ammonia enters the reactor system 100 from above as indicated by the arrow 11. Product stream exits the reactor system from the bottom thereof as indicated by the arrow 12.

Figure 1B:
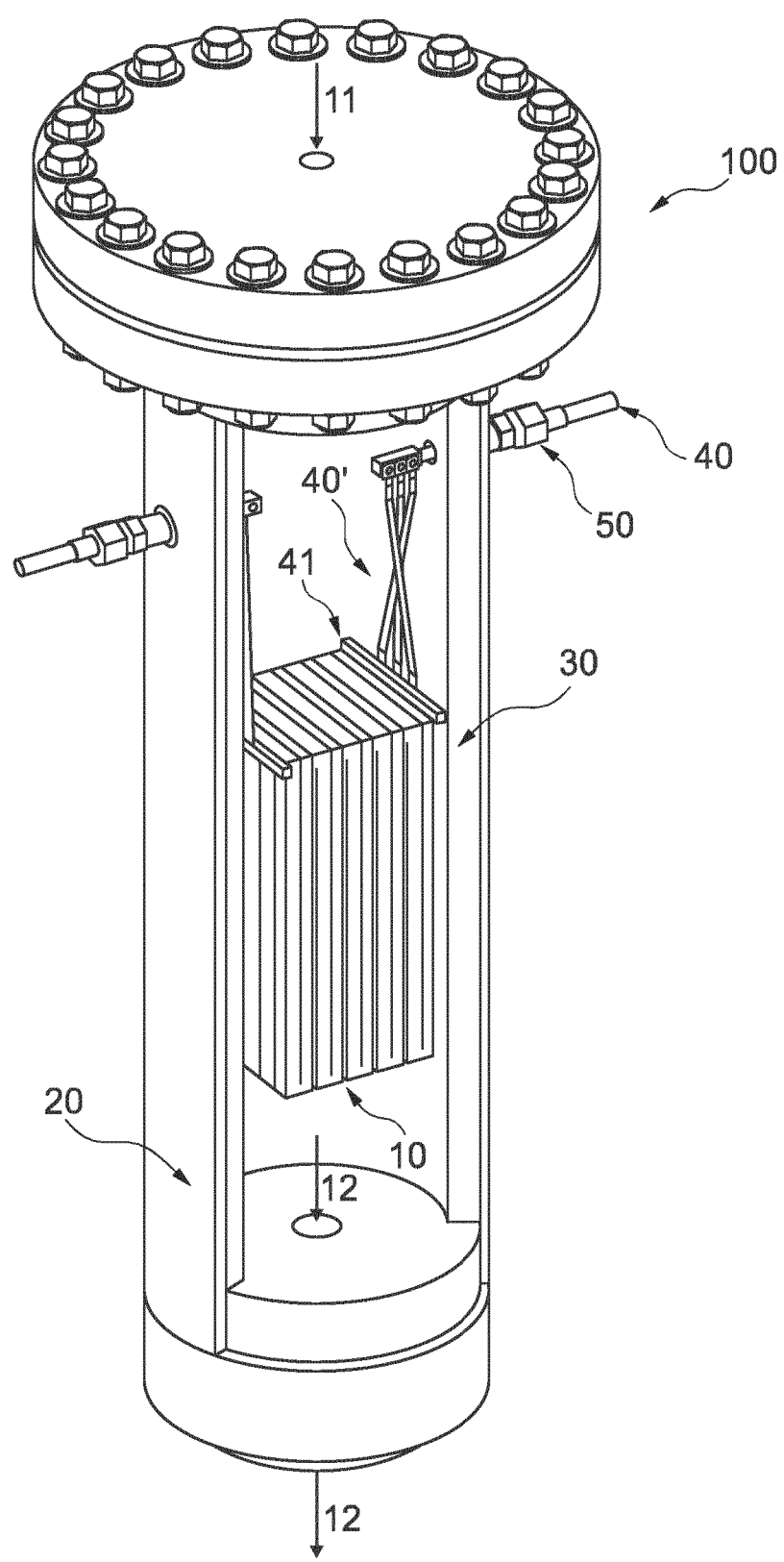
FIG. 1b shows the reactor system of FIG. 1a with a part of the pressure shell and heat insulation layer removed.
Figure 2:
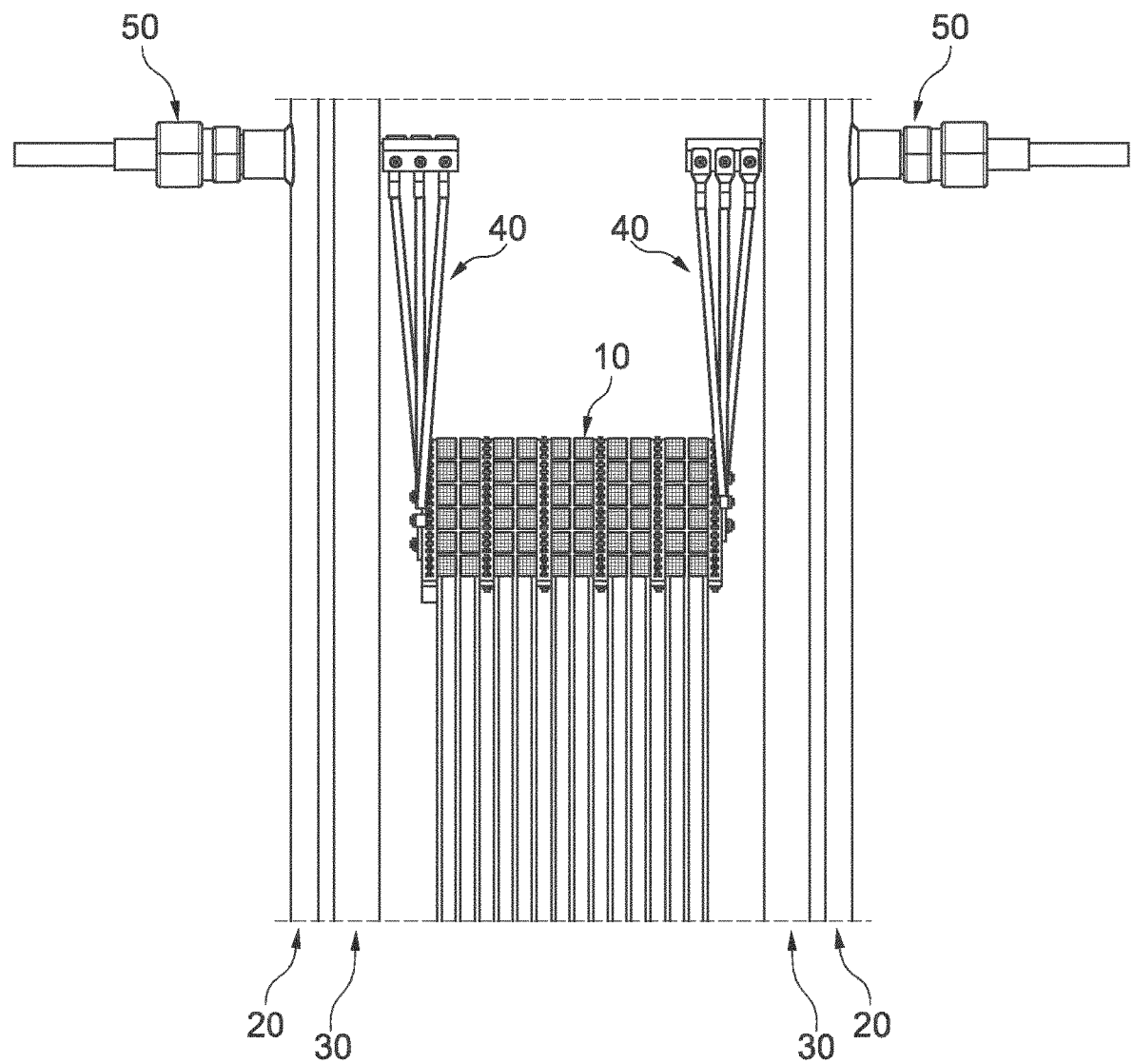
FIG. 2 is an enlarged view of a part of the reactor system.

FIG. 1b shows the reactor system 100 of FIG. 1a with a part of the pressure shell 20 and heat insulation 30 layer removed and FIG. 2 is an enlarged view of a part of the reactor system 100. In FIGS. 1b and 2 the connections between conductors 40' and conductor contact rails 41 are shown more clearly than in FIG. 1a. Moreover, it is seen that the conductors 40 are led through the walls of the pressure shell in a fitting 50, and that the one conductor 40 is split up into three conductors 40' within the pressure shell. It should be noted, that the number of conductors 40' may be any appropriate number, such as smaller than three or even larger than three.

In the reactor system shown in FIGS. 1a, 1b and 2, the conductors 40, 40' are led through the wall of a pressure shell 20 housing the structured catalyst and through insulating material 30 on the inner side of the pressure shell, via fittings 50. Feed gas for the BMA reaction is inlet into the reactor system 100 via an inlet in the upper side of the reactor system 100 as shown by the arrow 11, and converted product stream exits the reactor system 100 via an outlet in the bottom of the reactor system 100 as shown by the arrow 12. Moreover, one or more additional inlets (not shown in FIGS. 1a to 2) advantageously exist close to or in combination with the fittings 50. Such additional inlets allow a cooling gas to flow over, around, close to, or inside at least one conductor within the pressure shell to reduce the heating of the fitting. The cooling gas could e.g. be hydrogen, nitrogen, methane or mixtures thereof. The temperature of the cooling gas at entry into the pressure shell may be e.g. about 100° C.

In the reactor system 100 shown in FIGS. 1a to 2, inert material (not shown in FIGS. 1a-2) is advantageously present between the lower side of the structured catalyst 10 and the bottom of the pressure shell. Moreover, inert material is advantageously present between the outer sides of the structured catalyst 10 of macroscopic structures 5 and the insulating material 30. Thus, one side of the insulating material 30 faces the inner side of the pressure shell 20 and the other side of the insulating material 30 faces the inert material. The inert materiel is e.g. ceramic material and may be in the form of pellets. The inert material assists in controlling the pressure drop across the reactor system 100 and in controlling the flow of the gas through the reactor system 100, so that the gas flows over the surfaces of the structured catalyst 10.

FIGS. 3a and 3b show schematic cross sections through an embodiment of the inventive reactor system 100', 100" comprising a structured catalyst 10'. The structured catalyst 10' may consist of a single macroscopic structure with ceramic coating supporting catalytically active material or it may contain two or more macroscopic structures. Each of the reactor systems 100', 100" comprises a pressure shell 20 and a heat insulation layer 80 between the structured catalyst 10' and the pressure shell 20. Inert material 90 can be used to fill the gap between the structured catalyst 10' and the heat insulation layer or the pressure shell 20. In FIGS. 3a and 3b, the inert material 90 is indicated by dotted area; the inert material 90 may be in any appropriate form, e.g. in the form of inert pellets, and it is e.g. of ceramic material. The inert material 90 assists in controlling the pressure drop through the reactor system and in controlling the flow of the gas through the reactor system. Moreover, the inert material typically has a heat insulating effect.

From FIGS. 3a and 3b it is seen that the reactor systems 100', 100" further comprise an inner tube 15 in heat exchange relationship with the structured catalyst 10'. The inner tube 15 is adapted to withdraw a product gas from the structured catalyst 10' so that the product gas flowing through the inner tube or tubes is in heat exchange relationship with the gas flowing over the structured catalyst; however, the inner tube 15 is electrically insulated from the structured catalyst 10' by either a heat insulation layer 80, inert material 90, a gap, or a combination. This is a layout which is denoted a bayonet reactor system. In this layout, the product gas within the inner tube assists in heating the process gas flowing over the macroscopic structure. In the layouts shown in FIGS. 3a and 3b, the feed gas enters the reactor system 100', 100" as indicated by the arrow 11, and continues into the structured catalyst 10' as indicated by the arrows 13. During the passage of the feed gas over the structured catalyst 10', it undergoes the BMA reaction. The gas exiting the structured catalyst 10' is at least partly converted to hydrogen cyanide. The at least partly converted gas flows from the structured catalyst 10' into the inner tube 15 as indicated by the arrows 14, and exits the inner tube as indicated by the arrows 12. Even though the heat insulation layer 80 is present between the inner tube 15 and the structured catalyst 10', some heat transfer will take place from the gas within the inner tube 15 and the gas within the structured catalyst 10' or upstream the structured catalyst 10'. In the embodiments shown in FIGS. 3a and 3b, the feed gas flow downwards through the structured catalyst 10' and upwards through the inner tube 15; however, it is conceivable that the configuration was turned upside-down so that the feed gas would flow upwards through the structured catalyst 10' and downwards through the inner tube 15.

Figure 4:
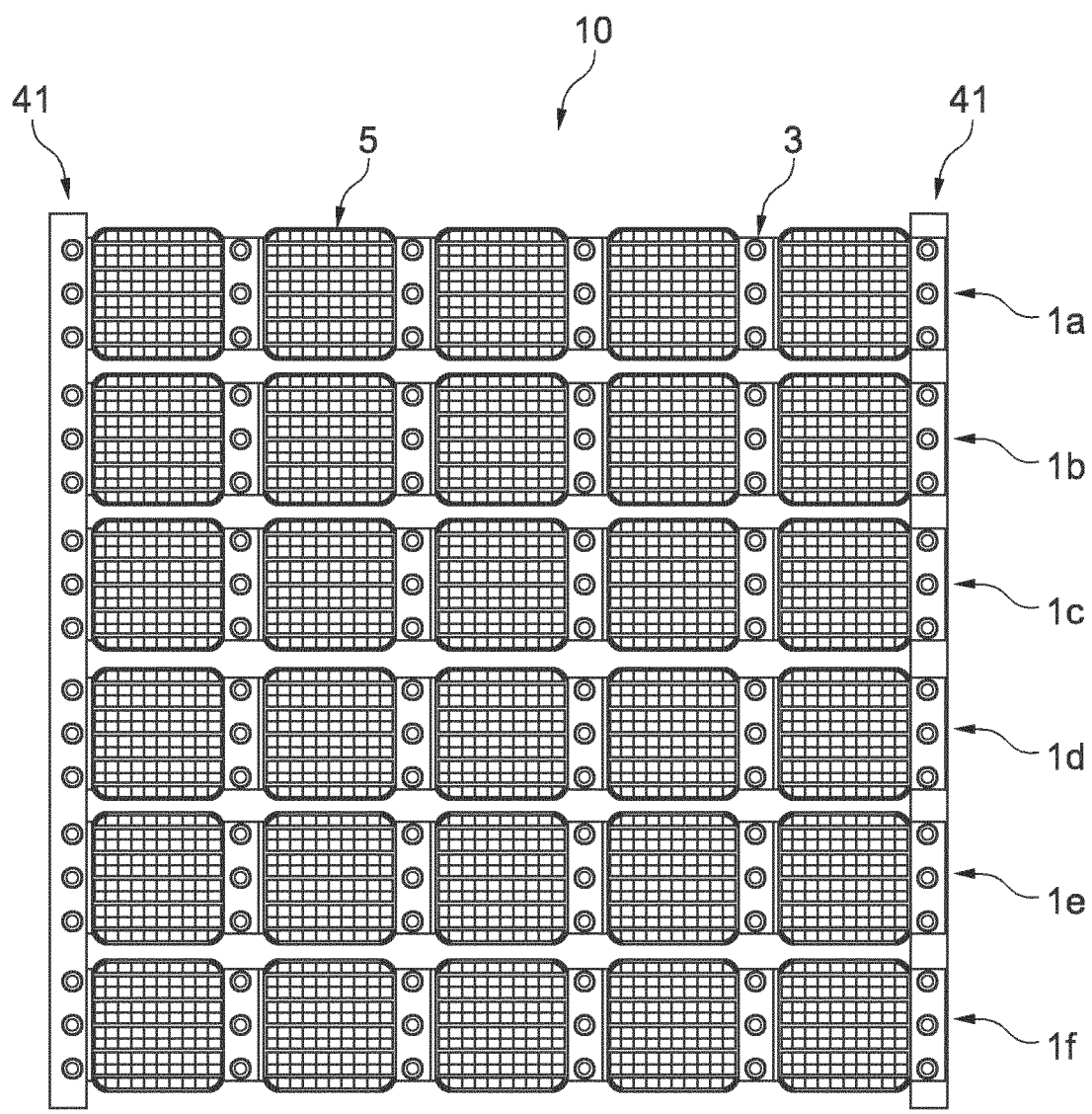
FIGS. 4 and 5 show an embodiment of a structured catalyst with an array of macroscopic structures as seen from above and from the side, respectively.
Figure 5:
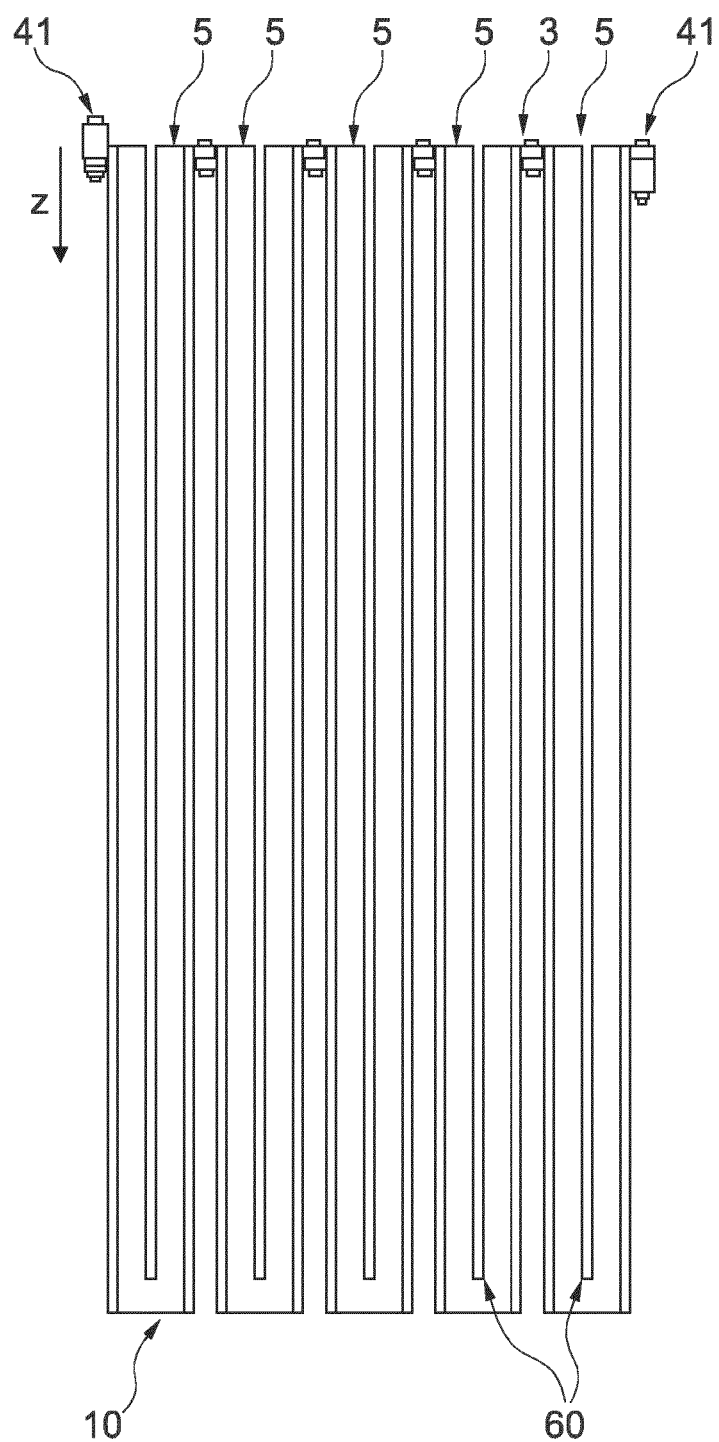

FIGS. 4 and 5 show an embodiment of a structured catalyst comprising an array of macroscopic structures as seen from above and from the side, respectively. FIG. 4 shows a structured catalyst 10 comprising an array of macroscopic structure 5 seen from above, viz. as seen from the arrow 11 in FIGS. 1a and 1b. The array has 6 rows, viz. 1a, 1b, 1c, 1d, 1e and 1f, of five macroscopic structures 5. The macroscopic structures 5 in each row are connected to its neighboring macroscopic structure (s) in the same row and the two outermost macroscopic structures in each row are connected to a conductor contact rail 41. The neighboring macroscopic structures 5 in a row of macroscopic structures are connected to each other by means of a connection piece 3.

FIG. 5 shows the structured catalyst 10 having an array of macroscopic structures 5 of FIG. 4 seen from the side. From FIG. 5, it can be seen that each macroscopic structure 5 extends longitudinally perpendicular to the cross section seen in FIG. 4. Each macroscopic structure 5 has a slit 60 cut into it along its longitudinal direction (see FIG. 5). Therefore, when energized by the power source, the current enters the array of macroscopic structures 5 via a conductor contact rail 41, is led through the first macroscopic structure 5 downwards until the lower limit of the slit 60 and is subsequently led upwards towards a connection piece 3. The current is led via a corresponding zigzag path, downwards and upwards, through each macroscopic structure 5 in each row 1a-1f of macroscopic structures 5 in the array 10. This configuration advantageously increases the resistance over the structured catalyst 10.

Figure 6:
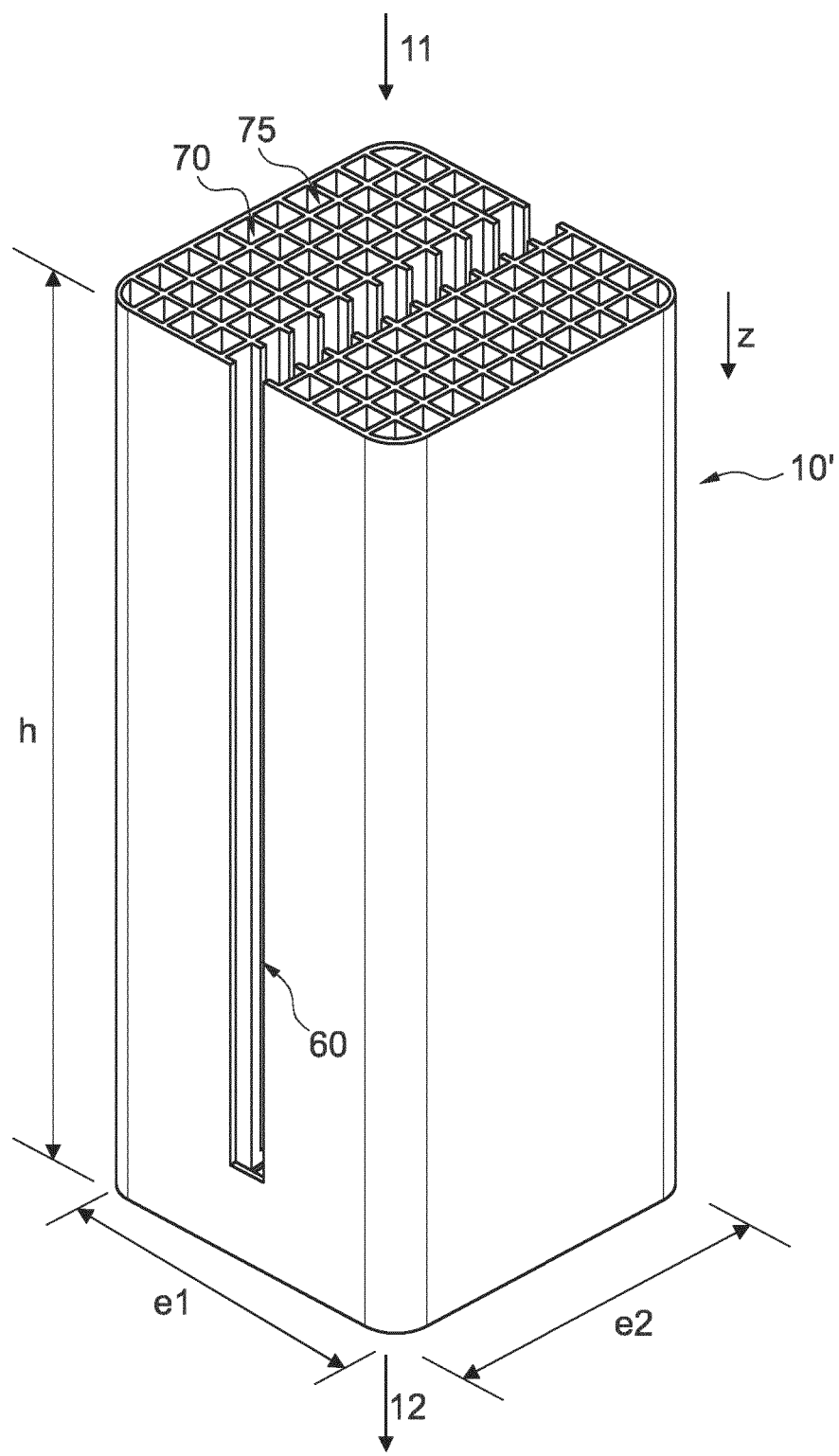
FIG. 6 shows an embodiment of the structured catalyst of the invention.

FIG. 6 shows a structured catalyst 10 according to the invention in a perspective view. The structured catalyst 10 comprises a macroscopic structure that is coated with a ceramic coating impregnated with catalytically active material. Within the structured catalyst are channels 70 extending along the longitudinal direction (shown by the arrow indicate 'h' in FIG. 6) of the macroscopic structure 5; the channels are defined by walls 75. In the embodiment shown in FIG. 6, the walls 75 define a number of parallel, square channels 70 when seen from the direction of flow as indicated by the arrow 12. The structured catalyst 10 has a substantially square perimeter when seen from above, defined by the edge lengths e1 and e2. However, the perimeter could also be circular or another shape.

The walls 75 of the structured catalyst 10 are of extruded or 3D printed material coated with a ceramic coating, e.g. an oxide, which has been coated onto the macroscopic structure. In the Figures, the ceramic coating is not shown. The ceramic coating is impregnated with catalytically active material. The ceramic coating and thus the catalytically active material are present on every wall within the structured catalyst 10 over which the gas flow flows during operation and interacts with the heated surface of the structured catalyst and the catalytically active material.

Thus, during use in a reactor system for the BMA reaction, a feed gas flows through the channels 70 and interacts with the heated surface of the structured catalyst and with the catalytically active material supported by the ceramic coating.

In the structured catalyst 10 shown in FIG. 6 a slit 60 has been cut into the structured catalyst 10. This slit 60 forces a current to take a zigzag route, in this instance downwards and subsequently upwards, within the macroscopic structure thereby increasing the current path and thus the resistance and consequently the heat dissipated within the macroscopic structure. The slit 60 within the macroscopic structure may be provided with embedded insulating material in order to ensure that no current flows in the transverse direction of the slit 60.

The channels 70 in the structured catalyst 10 are open in both ends. In use of the structured catalyst in a reactor system, a feed gas flows through the unit, in the direction shown by arrows 11 and 12 in FIGS. 1a and 1b, and gets heated via contact with the walls 75 of the channels 70 and by heat radiation. The heat initiates the desired BMA reaction. The walls 75 of the channels 70 may e.g. have a thickness of 0.5 mm, and the ceramic coating coated onto the walls 75 may e.g. have a thickness of 0.1 mm. Even though the arrows 11 and 12 (see FIGS. 1a and 1b) indicate that the flow of the feed gas is down-flow, the opposite flow direction, viz. an up-flow, is also conceivable.

Figure 7:
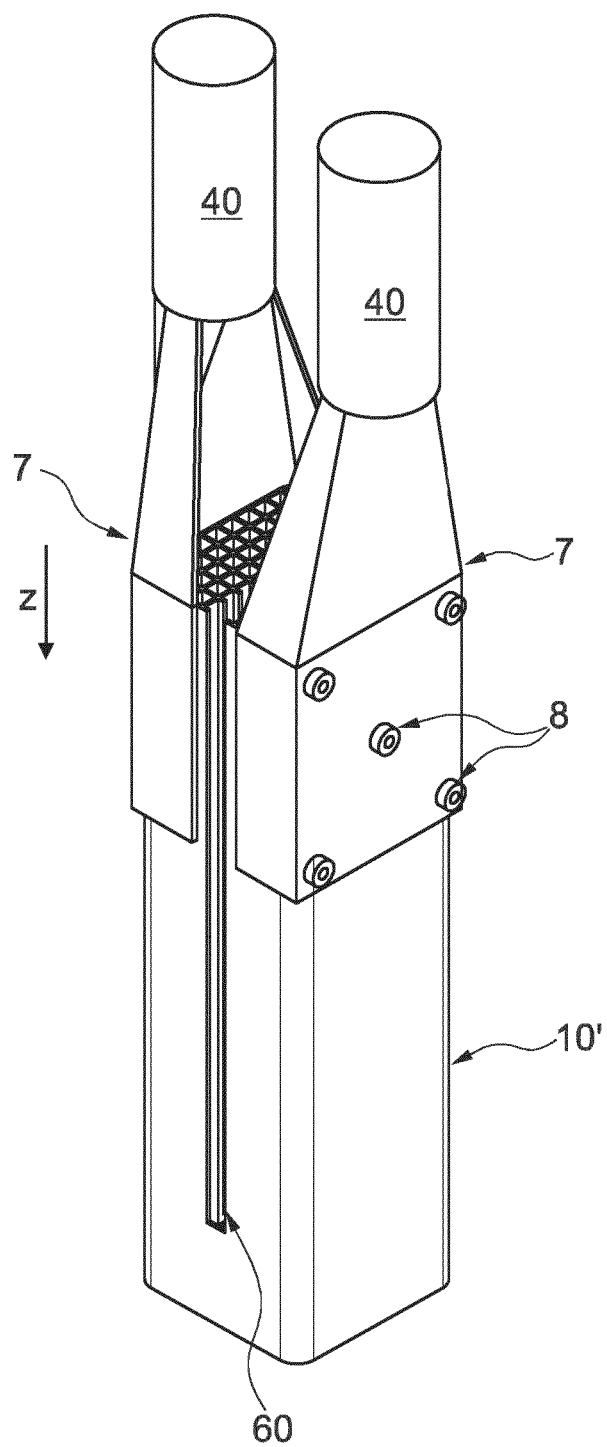
FIGS. 7 and 8 show embodiments of a structured catalyst with connectors.

FIG. 7 shows the structured catalyst 10 of FIGS. 1a and 1b in a perspective view and with connectors 7 attached. The connectors 7 each connect a part of the structured catalyst 10 to a conductor 40. The conductors 40 are both connected to a power supply (not shown). Each of the connectors 7 are connected to an upper part of the structured catalyst. When the conductors 40 are connected to a power supply, an electrical current is led to the corresponding connector 7 via the conductor and runs through the structured catalyst 10. The slit 60 hinders the current flow in a transverse direction (horizontal direction of FIG. 7) throughout its lengths along the height h of the structured catalyst 10. Therefore, the current runs in a direction downwards as seen in FIG. 7 in the part of the structured catalyst along the slit 60, subsequently it runs transversely to the longitudinal direction below the slit 60 as seen in FIG. 7 and finally the current runs upwards in the longitudinal direction of the structured catalyst to the other connector 7. The connectors 7 in FIG. 7 are mechanically fastened to the structured catalyst by means of inter alia mechanical fastening means such as screws and bolts. However, additional or alternative fastening means are conceivable. In an embodiment, the electrical power supply generates a voltage of 3V and a current of 400 A. The connectors 7 are e.g. made in materials like iron, aluminum, nickel, copper or alloys thereof.

As mentioned, the structured catalyst 10 is coated with a ceramic coating, such as an oxide, supporting the catalytically active material. However, the parts of the structured catalyst 10, which are connected to the connectors 7, should not be coated with an oxide. Instead, the macroscopic structure of the structured catalyst should be exposed or connected directly to the connectors 7 in order to obtain a good electrical connection between the macroscopic structure and the connector.

When the connectors 7 and thus the conductors 40 are connected to the same end of the structured catalyst 10, viz. the upper end as seen in FIG. 7, the feed gas entering into a reactor system housing the structured catalyst 10 would be able to cool the connectors 7 and the conductors 40. For instance, the feed gas entering into such a reactor system could have a temperature of 200° C. or 400° C. and would thus keep the connectors 7 and conductors 40 from reaching temperatures much higher than this temperature.

Figure 8:
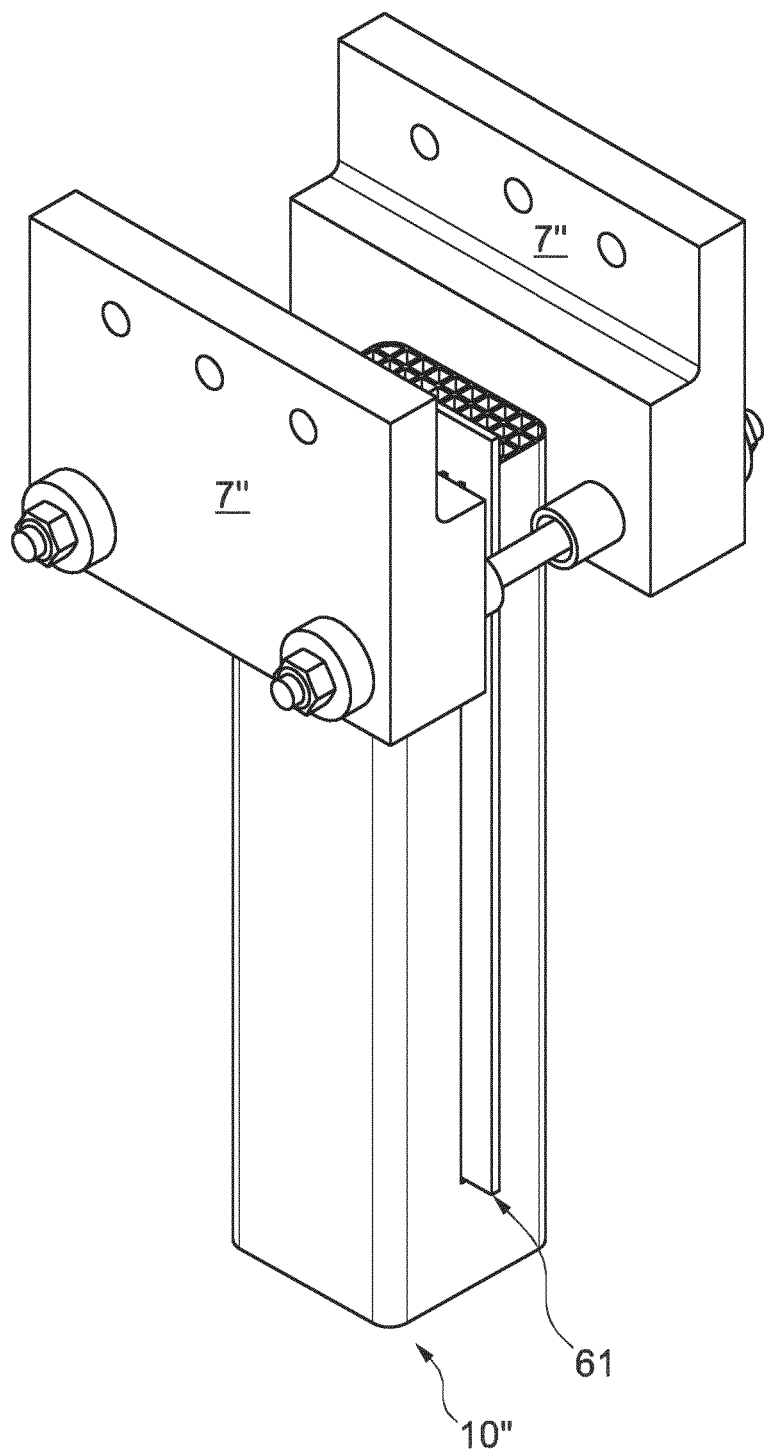

FIG. 8 shows another embodiment of a structured catalyst 10''' with connectors 7'''. The structured catalyst 10''' is e.g. the structured catalyst as shown in FIG. 6. Each of the connectors 7''' has three holes at an upper side thereof for connection to conductors (not shown). A piece of electrically insulating material 61 is inside the slit 60 (see FIG. 6) of the structured catalyst 10'''.

Figure 9:
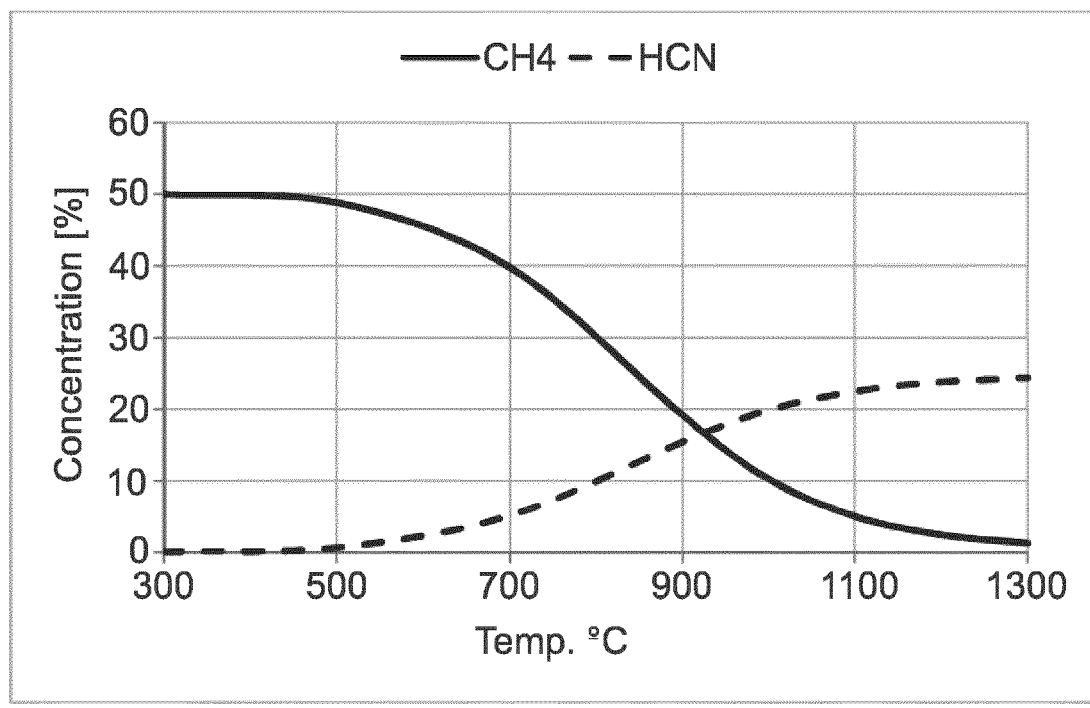
FIG. 9 shows the equilibrium composition of $CH_4$ (and $NH_3$) and HCN as a function of temperature at 5 barg when using an equimolar feed gas of $CH_4$ and $NH_3$.

FIG. 9 shows the equilibrium composition of $CH_4$ (and $NH_3$) vs HCN as a function of temperature at 5 barg when using an equimolar feed gas of $CH_4$ and $NH_3$. This illustrates thermodynamic equilibrium composition as a function of temperature. Notice, that only methane is shown as reactant, but as the feedgas is equimolar, this concentration is equivalent to the ammonia concentration due to the 1:1 stoichiometry. According to the figure, the reaction temperature should be above 1000° C. to have a high conversion of methane, where the remaining methane mole fraction still is 10.3%. Ideally, having a reaction temperature even higher of 1200° C. gives a resulting gas composition of 2.4% methane, 2.4% ammonia, and 23.8% hydrogen cyanide, with hydrogen as balance.

It should be noted, that even though the structured catalysts shown in the figures are shown as having channels with a square cross section, as seen perpendicular to the z axis, any appropriate shape of the cross sections of the channels is conceivable. Thus, the channels of the structured catalyst could alternatively be e.g. triangular, hexagonal, octagonal, or circular, where triangular, square, and hexagonal shapes are preferred.

While the invention has been illustrated by a description of various embodiments and examples while these embodiments and examples have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicant's general inventive concept.

ITEMS OF THE INVENTION

1. A reactor system for carrying out the reaction of a feed gas comprising an alkane and ammonia to hydrogen cyanide and/or a nitrile in the presence of a catalyst, said reactor system comprising:

a supply of feed gas comprising an alkane and ammonia;

a structured catalyst arranged for catalyzing the reaction of said feed gas, said structured catalyst comprising a macroscopic structure of an electrically conductive material, said macroscopic structure supporting a ceramic coating, wherein said ceramic coating supports a catalytically active material;

a pressure shell housing said structured catalyst, said pressure shell comprising an inlet for letting in said feed gas and an outlet for letting out product gas, wherein said inlet is positioned so that said feed gas enters said structured catalyst in a first end of said structured catalyst and said product gas exits said structured catalyst from a second end of said structured catalyst;

a heat insulation layer between said structured catalyst and said pressure shell;

at least two conductors electrically connected to said structured catalyst and to an electrical power supply placed outside said pressure shell, wherein said electrical power supply is dimensioned to heat at least part of said structured catalyst to a temperature of at least 500° C. by passing an electrical current through said macroscopic structure, wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors;

an outlet for a product stream comprising hydrogen cyanide and/or a nitrile.

2. The reactor system according to item 1, wherein said electrical power supply is dimensioned to heat at least part of said structured catalyst to a temperature of at least 700° C., preferably at least 900° C., more preferably at least 1000° C.

3. The reactor system according to any one of the preceding items, wherein the feed gas additionally comprises $H_2$, $N_2$, or Ar.

4. The reactor system according to any one of the preceding items, wherein the pressure shell has a design pressure of between 2 and 30 bar.

5. The reactor system according to any one of items 1-3, wherein the pressure shell has a design pressure of between 30 and 200 bar.

6. The reactor system according to any one of the preceding items, wherein the resistivity of the electrically conductive material is between $10^{-5}$ $\Omega \cdot m$ and $10^{-7}$ $\Omega \cdot m$.

7. The reactor system according to any one of the preceding items, where said at least two conductors are led through the pressure shell in a fitting so that the at least two conductors are electrically insulated from the pressure shell.

8. The reactor system according to item 7, wherein said pressure shell further comprises one or more inlets close to or in combination with at least one fitting in order to allow a cooling gas to flow over, around, close to, or inside at least one conductor within said pressure shell.

9. The reactor system according to any one of the preceding items, wherein the reactor system further comprises an inner tube in heat exchange relationship with but electrically insulated from the structured catalyst, said inner tube being adapted to withdraw a product gas from the structured catalyst so that the product gas flowing through the inner tube is in heat exchange relationship with gas flowing over the structured catalyst.

10. The reactor system according to any one of the preceding items, wherein the connection between the structured catalyst and said at least two conductors is a mechanical connection, a welded connection, a brazed connection or a combination thereof.

11. The reactor system according to any one of the preceding items, wherein the electrically conductive material comprises a 3D printed or extruded and sintered macroscopic structure, said macroscopic structure is supporting a ceramic coating, wherein said ceramic coating supports a catalytically active material.

12. The reactor system according to any one of the preceding items, wherein the structured catalyst comprises an array of macroscopic structures electrically connected to each other.

13. The reactor system according to any of the preceding items, wherein said structured catalyst has electrically insulating parts arranged to increase the length of a principal current path between said at least two conductors to a length larger than the largest dimension of the structured catalyst.

14. The reactor system according to any of the preceding items, wherein said structured catalyst has at least one electrically insulating part arranged to direct a current through said structured catalyst in order to ensure that for at least 70% of the length of said structured catalyst, a current density vector of the principal current path has a non-zero component value parallel to the length of said structured catalyst.

15. The reactor system according to any one of the preceding items, wherein said macroscopic structure has a plurality of parallel channels, a plurality of non-parallel channels and/or a plurality of labyrinthic channels.

16. The reactor system according to any one of the preceding items, wherein said reactor system further comprises a third catalyst material in the form of catalyst pellets, extrudates or granulates loaded into the channels of said macroscopic structure.

17. The reactor system according to any one of the preceding items, wherein the reactor system further comprises a bed of a fourth catalyst material downstream said structured catalyst within said pressure shell.

18. The reactor system according to any one of the preceding items, wherein the material of the macroscopic structure is chosen as a material arranged to generate a heat flux of 500 to 50000 $W/m^2$ by resistance heating of the material.

19. The reactor system according to any one of the preceding items, wherein the structured catalyst comprises a first part arranged to generate a first heat flux and a second part arranged to generate a second heat flux, where the first heat flux is lower than the second heat flux, and where the first part is upstream the second part.

20. The reactor system according to any one of the preceding items, wherein the structured catalyst comprises a third part arranged to generate a third heat flux, where the third heat flux is lower than the first and/or the second heat flux, and where the third part is downstream the first and/or second part.

21. The reactor system according to any one of the preceding items, wherein said reactor system further comprises a control system arranged to control the electrical power supply to ensure that the temperature of the gas exiting the pressure shell lies in a predetermined range and/or to ensure that the conversion of the feed gas lies in a predetermined range.

22. The reactor system according to any one of the preceding items, wherein the structured catalyst within said reactor system has a ratio between the area equivalent diameter of a horizontal cross section through the structured catalyst and the height of the structured catalyst in the range from 0.1 to 2.0.

23. The reactor system according to any one of the preceding items, wherein the height of the reactor system is between 0.5 and 7 m, more preferably between 0.5 and 3 m.

24. The reactor system according to any one of the preceding items, wherein the alkane is methane, the catalyst is a BMA catalyst and the product stream comprises hydrogen cyanide.

25. A process for carrying out the reaction of a feed gas comprising an alkane and ammonia to hydrogen cyanide and/or a nitrile in the presence of a catalyst, in a reactor system comprising a pressure shell housing a structured catalyst arranged for catalyzing said endothermic reaction of a feed gas, said structured catalyst comprising a macroscopic structure of electrically conductive material, said macroscopic structure supporting a ceramic coating, wherein said ceramic coating supports a catalytically active material; wherein said reactor system is provided with heat insulation between said structured catalyst and said pressure shell; said process comprising the steps of:

pressurizing said feed gas, supplying said pressurized feed gas to said pressure shell through an inlet positioned so that said feed gas enters said structured catalyst in a first end of said structured catalyst; allowing the feed gas to undergo reaction over the structured catalyst and outletting a product gas from said pressure shell, wherein said product gas exits said structured catalyst from a second end of said structured catalyst;

supplying electrical power via electrical conductors connecting an electrical power supply placed outside said pressure shell to said structured catalyst, allowing an electrical current to run through said macroscopic structure, thereby heating at least part of the structured catalyst to a temperature of at least 500° C., wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors, thereby heating at least part of the structured catalyst to a temperature sufficient for said feed gas to undergo the BMA reaction over the structured catalyst, thereby heating at least part of the structured catalyst to a temperature sufficient for said feed gas to undergo the BMA reaction over the structured catalyst, outletting a product gas comprising hydrogen cyanide and/or a nitrile from the reactor system.

26. The process according to item 25, wherein said feed gas is pressurised to a pressure between 2 and 30 bar.

27. The process according to item 25 wherein said feed gas is pressurised to a pressure between 30 and 200 bar 28. The process according to any one of items 25 to 27, wherein at least part of the structured catalyst is heated to a temperature of at least 700° C., preferably at least 900° C., more preferably at least 1000° C.

29. The process according to any one of items 25 to 28, further comprising the step of inletting a cooling gas through an inlet through the pressure shell in order to allow said cooling gas to flow over at least one conductor.

30. The process according to any one of items 25-29, wherein the alkane is methane, the catalyst is a BMA catalyst and the product stream comprises hydrogen cyanide.

31. The process according to claim 30, wherein the process further comprises the step of feeding the product stream comprising hydrogen cyanide to an upgrading unit and separating it into an upgraded hydrogen cyanide stream and an off-gas stream.

32. The process according to item 31, wherein the upgrading unit is arranged so that the off-gas stream is recycled and mixed with the supply of feed gas before being passed over the structured catalyst 33. The process according to item 31 or 32, wherein the process further comprises the step of feeding the upgraded hydrogen cyanide stream from said upgrading unit to a downstream plant for HCN conversion to an upgraded product and where the production of HCN is equivalent to the consumption of HCN in the downstream plant.

34. A method for rapidly switching a metal-catalysed reaction of a feed gas comprising an alkane and ammonia in a reactor system according to any one of claims 1-24, from a first steady-state reaction condition (A) to a second steady-state reaction condition (B) or vice-versa; said method comprising the steps of:

in said first steady-state reaction condition (A):

supplying said feed gas to the reactor system in a first total flow, and supplying a first electrical power via electrical conductors connecting an electrical power supply placed outside said pressure shell to said structured catalyst, thereby allowing a first electrical current to run through said electrically conductive material, thereby heating at least part of the structured catalyst to a first temperature at which said feed gas is converted to a first product gas mixture over said structured catalyst under said first steady-state reaction conditions (A); and said first product gas is outlet from the reactor system;

and, in said second steady-state reaction condition (B):

supplying said feed gas to the reactor system in a second total flow, supplying a second electrical power via electrical conductors connecting an electrical power supply placed outside said pressure shell to said structured catalyst, thereby allowing a second electrical current to run through said electrically conductive material, thereby heating at least part of the structured catalyst to a second temperature; at which said feed gas is converted to a second product gas mixture over said structured catalyst under said second steady-state reaction conditions (B); and said second product gas is outlet from the reactor system;

wherein said second electrical power is higher than said first electrical power; and/or said second total flow is higher than said first total flow.

35. The method according to item 34, wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors.

36. The method according to any one of items 34-35, wherein the ratio of total gas feed flow in said first reaction condition A to said second reaction condition B (A:B) is at least 1:10.

37. The method according to any one of items 34-36, wherein the product gas outlet temperature from the structured catalyst in reaction condition B is between 50° C. to 800° C. higher, such as between 100° C. to 500° C. higher, preferably between 150° C. to 400° C. higher than the product gas outlet temperature from the structured catalyst in reaction condition A.

38. The method according to any one of items 34-37, wherein the switch between reaction condition A and B includes a gradual change of the total gas feed flow from said first total flow to said second total flow and simultaneous gradual change of the applied electrical potential over said electrically conductive material from said first to said second electrical power.

39. The method according to any one of items 34-38, wherein the product gas outlet temperature from the structured catalyst in reaction condition B is no more than 50° C. higher than the product gas outlet temperature from the structured catalyst in reaction condition A.

40. The method according to any one of items 34-39, wherein a proportional-integral-derivative (PID) controller controls the electrical potential based on feedback reading of the process value of product gas outlet temperature from the structured catalyst.

41. The method according to any one of items 34-40, wherein the product gas outlet temperature from the structured catalyst is measured directly beneath or on the most downstream surface of the structured catalyst.

42. The method according to any one of items 34-41, wherein the switch between reaction condition A and B takes place over a period of less than 3 hours, such as less than 2 hours, such as less than 60 min, preferably less than 30 min, and even more preferably less than 15 min.

43. The method according to any one of items 34-42, wherein the switch between reaction condition A and B involves supplying a second electrical power to the structured catalyst.

44. The method according to any one of items 34-43, wherein the switch between reaction condition A and B comprises a transition state between said reaction conditions A and B; said transition state comprising a first period in which the electrical power is switched off, followed by a second period in which said second electrical power of condition B is supplied to the structured catalyst.

45. The method according to any one of items 34-44, wherein the switch between reaction condition A and B comprises a transition state between said reaction conditions A and B; said transition state comprising a first period in which a third electrical power is supplied to the structured catalyst, followed by a second period in which said second electrical power of condition B is supplied to the structured catalyst, said third electrical power being higher than the second electrical power.

The invention claimed is:

1. A reactor system for carrying out the reaction of a feed gas comprising an alkane and ammonia to hydrogen cyanide and/or a nitrile in the presence of a catalyst, said reactor system comprising:
a supply of feed gas comprising an alkane and ammonia;
a structured catalyst arranged for catalyzing the reaction of said feed gas, said structured catalyst comprising a macroscopic structure of an electrically conductive material, said macroscopic structure supporting a ceramic coating, wherein said ceramic coating supports a catalytically active material;
a pressure shell housing said structured catalyst, said pressure shell comprising an in-let for letting in said feed gas and an outlet for letting out product gas, wherein said inlet is positioned so that said feed gas enters said structured catalyst in a first end of said structured catalyst and said product gas exits said structured catalyst from a second end of said structured catalyst;
a heat insulation layer between said structured catalyst and said pressure shell;
at least two conductors electrically connected to said structured catalyst and to an electrical power supply placed outside said pressure shell, wherein said electrical power supply is dimensioned to heat at least part of said structured catalyst to a temperature of at least 500° C. by passing an electrical current through said macroscopic structure, wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors;
an outlet for a product stream comprising hydrogen cyanide and/or a nitrile.

2. The reactor system according to claim 1, wherein said electrical power supply is dimensioned to heat at least part of said structured catalyst to a temperature of at least 700° C.

3. The reactor system according to claim 1, wherein the feed gas additionally comprises $H_2$, $N_2$, or Ar.

4. The reactor system according to claim 1, wherein the pressure shell has a design pressure of between 2 and 30 bar.

5. A method for rapidly switching a metal-catalysed reaction of a feed gas comprising an alkane and ammonia in a reactor system according to claim 1, from a first steady-state reaction condition (A) to a second steady-state reaction condition (B) or vice-versa; said method comprising the steps of:
in said first steady-state reaction condition (A):
supplying said feed gas to the reactor system in a first total flow, and
supplying a first electrical power via electrical conductors connecting an electrical power supply placed outside said pressure shell to said structured catalyst, thereby allowing a first electrical current to run through said electrically conductive material, thereby heating at least part of the structured catalyst to a first temperature at which said feed gas is converted to a first product gas mixture over said structured catalyst under said first steady-state reaction conditions (A); and said first product gas is outlet from the reactor system;
and, in said second steady-state reaction condition (B):
supplying said feed gas to the reactor system in a second total flow,
supplying a second electrical power via electrical conductors connecting an electrical power supply placed outside said pressure shell to said structured catalyst, thereby allowing a second electrical current to run through said electrically conductive material, thereby heating at least part of the structured catalyst to a second temperature; at which said feed gas is converted to a second product gas mixture over said structured catalyst under said second steady-state reaction conditions (B); and said second product gas is outlet from the reactor system;

wherein said second electrical power is higher than said first electrical power; and/or said second total flow is higher than said first total flow.

6. A process for carrying out the reaction of a feed gas comprising an alkane and ammonia to hydrogen cyanide and/or a nitrile in the presence of a catalyst, in a reactor system comprising a pressure shell housing a structured catalyst arranged for catalyzing said endothermic reaction of a feed gas, said structured catalyst comprising a macroscopic structure of electrically conductive material, said macroscopic structure supporting a ceramic coating, wherein said ceramic coating supports a catalytically active material; wherein said reactor system is provided with heat insulation between said structured catalyst and said pressure shell; said process comprising the steps of:

pressurizing said feed gas, supplying said pressurized feed gas to said pressure shell through an inlet positioned so that said feed gas enters said structured catalyst in a first end of said structured catalyst;

allowing the feed gas to undergo reaction over the structured catalyst and outletting a product gas from said pressure shell, wherein said product gas exits said structured catalyst from a second end of said structured catalyst;

supplying electrical power via electrical conductors connecting an electrical power supply placed outside said pressure shell to said structured catalyst, allowing an electrical current to run through said macroscopic structure, thereby heating at least part of the structured catalyst to a temperature of at least 500° C., wherein said at least two conductors are connected to the structured catalyst at a position on the structured catalyst closer to said first end of said structured catalyst than to said second end of said structured catalyst, and wherein the structured catalyst is constructed to direct an electrical current to run from one conductor substantially to the second end of the structured catalyst and return to a second of said at least two conductors, thereby heating at least part of the structured catalyst to a temperature sufficient for said feed gas to undergo the BMA reaction over the structured catalyst, thereby heating at least part of the structured catalyst to a temperature sufficient for said feed gas to undergo the BMA reaction over the structured catalyst, outletting a product gas comprising hydrogen cyanide and/or a nitrile from the reactor system.

7. The process according to claim 6, wherein the alkane is methane, the catalyst is a BMA catalyst and the product stream comprises hydrogen cyanide.

8. The process according to claim 7, wherein the process further comprises the step of feeding the product stream comprising hydrogen cyanide to an upgrading unit and separating it into an upgraded hydrogen cyanide stream and an off-gas stream.

9. The process according to claim 8, wherein the upgrading unit is arranged so that the off-gas stream is recycled and mixed with the supply of feed gas before being passed over the structured catalyst.

10. The process according to claim 8, wherein the process further comprises the step of feeding the upgraded hydrogen cyanide stream from said upgrading unit to a downstream plant for HCN conversion to an upgraded product and where the production of HCN is equivalent to the consumption of HCN in the downstream plant.

* * * * *